US011225645B2

(12) United States Patent
Omura et al.

(10) Patent No.: US 11,225,645 B2
(45) Date of Patent: *Jan. 18, 2022

(54) COENZYME-BINDING GLUCOSE DEHYDROGENASE

(71) Applicants: Ikeda Food Research Co., Ltd., Fukuyama (JP); PHC Corporation, Ehime (JP)

(72) Inventors: Hironori Omura, Hiroshima (JP); Hirokazu Sanada, Hiroshima (JP); Takako Yada, Hiroshima (JP); Tetsunari Morita, Hiroshima (JP); Mika Kuyama, Hiroshima (JP); Tokuji Ikeda, Kyoto (JP); Kenji Kano, Kyoto (JP); Seiya Tsujimura, Nara (JP)

(73) Assignees: Ikeda Food Research Co., Ltd., Fukuyama (JP); PHC Corporation, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/278,019

(22) Filed: Feb. 15, 2019

(65) Prior Publication Data
US 2019/0177699 A1 Jun. 13, 2019

Related U.S. Application Data

(60) Continuation of application No. 12/851,668, filed on Aug. 6, 2010, now abandoned, which is a continuation of application No. 12/396,724, filed on Mar. 3, 2009, now abandoned, which is a division of application No. 10/540,025, filed as application No. PCT/JP03/16603 on Dec. 24, 2003, now Pat. No. 7,514,250.

(30) Foreign Application Priority Data

Dec. 24, 2002 (JP) ................. 2002-373297

(51) Int. Cl.
C12N 9/04 (2006.01)
C12Q 1/32 (2006.01)
C12Q 1/54 (2006.01)
C12N 9/02 (2006.01)
A61K 38/00 (2006.01)

(52) U.S. Cl.
CPC ............ C12N 9/0004 (2013.01); C12Q 1/32 (2013.01); C12Q 1/54 (2013.01)

(58) Field of Classification Search
CPC .......................... C12Q 1/006; C12Y 101/9901
See application file for complete search history.

(56) References Cited

U.S. PATENT DOCUMENTS 4,767,785 A  8/1988  Georgieff et al.
5,120,420 A  6/1992  Nankai et al.
5,286,362 A  2/1994  Hoenes et al.
5,413,690 A  5/1995  Kost et al.
5,602,018 A  2/1997  Kopetzki et al.
5,762,770 A  6/1998  Pritchard et al.
6,059,946 A * 5/2000  Yukawa ................. C12Q 1/001
                                                  204/403.14
6,071,391 A  6/2000  Gotoh et al.
6,100,037 A  8/2000  Phillips et al.
6,103,509 A  8/2000  Sode et al.
6,338,790 B1  1/2002  Feldman et al.
6,558,920 B1  5/2003  Hata et al.
6,592,745 B1  7/2003  Feldman et al.
(Continued)

FOREIGN PATENT DOCUMENTS

DE  43 01 904 A1  2/1994
EP  0 094 161 A1  11/1983
(Continued)

OTHER PUBLICATIONS

Komori et al. (2015) Crystallographic analysis of FAD-dependent glucose dehydrogenase; Struct. Biol. Commun., vol. F71, pp. 1017-1019.*
Bak et al., "Studies on glucose dehydrogenase of Aspergillus oryzae," Biochimica et Biophysica Acta, 146: 328-335 (1967).
Bak, "Studies on Glucose Dehydrogenase of Aspergillus Oryzae III. General Enzymatic Properties," Biochimica et Biophysica Acta, 146: 317-327 (1967).
Bak, "Studies on Glucose Dehydrogenase of Aspergillus Oryzae II, Purification and Physical and Chemical Properties," Biochimica et Biophysica Acta, 146: 277-293 (1967).
Cozier et al., "Characterization of the membrane quinoprotein glucose dehydrogenase from *Escherichia coli* and characterization of a site-directed mutant in which histidine-262 has been changed to tyrosine," Biochem. J., 340: 639-647 (1999).
(Continued)

*Primary Examiner* — Manjunath N Rao
*Assistant Examiner* — Samuel W Liu
(74) *Attorney, Agent, or Firm* — Amster, Rothstein & Ebenstein LLP

(57) ABSTRACT

The present invention provides a microorganism-derived soluble coenzyme-binding glucose dehydrogenase which catalyzes a reaction for oxidizing glucose in the presence of an electron acceptor, has an activity to maltose as low as 5% or less, and is inhibited by 1,10-phenanthroline. The invention also provides a method for producing the coenzyme-binding glucose dehydrogenase, and a method and a reagent for measuring employing the coenzyme-binding glucose dehydrogenase, According to the invention, the coenzyme-binding glucose dehydrogenase can be applied to an industrial field, and a use becomes possible also in a material production or analysis including a method for measuring or eliminating glucose in a sample using the coenzyme-binding glucose dehydrogenase as well as a method for producing an organic compound. It became also possible to provide a glucose sensor capable of accurately measuring a blood sugar level. Therefore, it became possible to provide an enzyme having a high utility, such as an ability of being used for modifying a material in the fields of pharmaceuticals, clinical studies and food products.

2 Claims, 6 Drawing Sheets

(56) References Cited

U.S. PATENT DOCUMENTS

| | | | |
|---|---|---|---|
| 6,656,702 B1 * | 12/2003 | Yugawa | C12Q 1/005 205/777.5 |
| 6,773,564 B1 | 8/2004 | Yugawa et al. | |
| 7,005,048 B1 | 2/2006 | Watanabe et al. | |
| 7,049,114 B1 | 5/2006 | Sode et al. | |
| 7,067,295 B1 | 6/2006 | Sode et al. | |
| 7,132,270 B2 | 11/2006 | Kratzsch et al. | |
| 7,244,600 B2 | 7/2007 | Sode et al. | |
| 7,276,146 B2 | 10/2007 | Wilsey | |
| 7,514,250 B2 | 4/2009 | Omura et al. | |
| 7,553,649 B2 | 6/2009 | Tsuji et al. | |
| 7,655,130 B2 | 2/2010 | Tsuji et al. | |
| 7,741,090 B2 | 6/2010 | Sode et al. | |
| 8,492,130 B2 | 7/2013 | Yada et al. | |
| 8,691,547 B2 | 4/2014 | Omura et al. | |
| 8,882,978 B2 | 11/2014 | Yada et al. | |
| 9,328,372 B2 | 5/2016 | Omura et al. | |
| 9,340,816 B2 | 5/2016 | Yada et al. | |
| 9,663,811 B2 | 5/2017 | Yada et al. | |
| 9,957,543 B2 | 5/2018 | Omura et al. | |
| 9,976,125 B2 | 5/2018 | Yada et al. | |
| 10,648,011 B2 | 5/2020 | Omura et al. | |
| 10,669,565 B2 | 6/2020 | Omura et al. | |
| 2003/0082595 A1 | 5/2003 | Jiang et al. | |
| 2003/0175841 A1 | 9/2003 | Watanabe et al. | |
| 2004/0266009 A1 * | 12/2004 | Shuster | C12N 9/20 435/471 |
| 2006/0019328 A1 | 1/2006 | Sode | |
| 2006/0063217 A1 | 3/2006 | Omura et al. | |
| 2007/0105173 A1 | 5/2007 | Takeshima et al. | |
| 2008/0014612 A1 | 1/2008 | Tsuji et al. | |
| 2008/0206833 A1 | 8/2008 | Yamaoka et al. | |
| 2008/0248514 A1 | 10/2008 | Inamori et al. | |
| 2009/0181408 A1 | 7/2009 | Tanaka et al. | |
| 2009/0259024 A1 | 10/2009 | Tsuji et al. | |
| 2010/0135977 A1 | 6/2010 | Palczewski et al. | |
| 2010/0323378 A1 | 12/2010 | Honda et al. | |
| 2011/0033880 A1 | 2/2011 | Yada et al. | |
| 2013/0332133 A1 * | 12/2013 | Horn | C12N 9/00 703/11 |
| 2016/0076007 A1 | 3/2016 | Omura et al. | |
| 2016/0273018 A1 | 9/2016 | Omura et al. | |
| 2017/0136102 A1 * | 5/2017 | Sharma | A61K 38/162 |

FOREIGN PATENT DOCUMENTS

| | | | | |
|---|---|---|---|---|
| EP | 0094161 A1 * | 11/1983 | | C12N 9/0006 |
| EP | 0 992 589 A2 | 4/2000 | | |
| EP | 1 152 239 A1 | 11/2001 | | |
| EP | 1 167 519 A1 | 1/2002 | | |
| EP | 1 176 202 B1 | 1/2002 | | |
| EP | 1 584 675 A1 | 10/2005 | | |
| EP | 1 739 174 A1 | 1/2007 | | |
| EP | 1 862 543 A1 | 12/2007 | | |
| EP | 2 003 199 A1 | 12/2008 | | |
| EP | 2 380 980 A1 | 10/2011 | | |
| EP | 2 380 980 B1 | 11/2014 | | |
| JP | 59-025700 A | 2/1984 | | |
| JP | 1988-139243 | 6/1988 | | |
| JP | 1988-139244 | 6/1988 | | |
| JP | 1988-317757 | 12/1988 | | |
| JP | 1992-215055 | 8/1992 | | |
| JP | 1993-215711 | 8/1993 | | |
| JP | 1993-196595 | 8/1996 | | |
| JP | 1998-505421 | 5/1998 | | |
| JP | 10-239273 | 9/1998 | | |
| JP | 10-243786 A | 9/1998 | | |
| JP | 2000-262281 A | 9/2000 | | |
| JP | 2000-312588 A | 11/2000 | | |
| JP | 2000-350588 A | 12/2000 | | |
| JP | 2000-354495 A | 12/2000 | | |
| JP | 2001-037483 A | 2/2001 | | |
| JP | 2001-046078 A | 2/2001 | | |
| JP | 2001-197888 A | 7/2001 | | |
| JP | 2001-346587 A | 12/2001 | | |
| JP | 2002-223772 A | 8/2002 | | |
| JP | 2002-526759 A | 8/2002 | | |
| JP | 2004-512047 A | 4/2004 | | |
| JP | 2004-173538 A | 6/2004 | | |
| JP | 2004-313172 A | 11/2004 | | |
| JP | 2004-313180 A | 11/2004 | | |
| JP | 2004-329143 A | 11/2004 | | |
| JP | 2004-344145 A | 12/2004 | | |
| JP | 2005-089884 | 4/2005 | | |
| JP | 2006-091022 A | 4/2006 | | |
| JP | 2007-289148 A | 11/2007 | | |
| JP | 2008-154572 A | 7/2008 | | |
| JP | 2008-178380 A | 8/2008 | | |
| JP | 2008-206433 A | 9/2008 | | |
| WO | WO 98/20136 A1 | 5/1998 | | |
| WO | WO 02/34919 A1 | 5/2002 | | |
| WO | WO 02/36779 A1 | 5/2002 | | |
| WO | WO 02/072839 A1 | 9/2002 | | |
| WO | WO 03/012071 A2 | 2/2003 | | |
| WO | WO 2004/058958 A1 | 7/2004 | | |
| WO | WO 2005/088288 A1 | 9/2005 | | |
| WO | WO 2005/103248 A1 | 11/2005 | | |
| WO | WO 2006/101239 A1 | 9/2006 | | |
| WO | WO 2007/139013 A1 | 12/2007 | | |
| WO | WO 2015/060150 A1 | 4/2015 | | |

OTHER PUBLICATIONS

European Search Report issued for application No. EP 11156659.2, dated Jun. 28, 2011.

European Search Report issued for application No. EP 11156661.8, dated Jun. 6, 2011.

European Search Report issued for application No. EP 11156657.6, dated Aug. 25, 2011.

European Search Report issued for application No. EP 11156649.3, dated Sep. 23, 2011.

European Search Report issued for application No. EP 11156664.2, dated Sep. 23, 2011.

Hayano et al., "Purification and Properties of 3-Ketosucrose-forming Enzyme from the Cells of Agrobacterium tumefaciens," J. of Biol. Chem., 242: 3665-3672 (1967).

Kojima et al., "Fundamental study for an oxygen-insensitive amperometric glucose sensor using a novel glucose dehydrogenase," Chemical Sensors, 20: 768-769 (2004).

Morrison et al., "Characterization of a glucose 3-dehydrogenase from the cultivated mushroom (Aqaricus bisporus)," Appl. Microbial Biotechnol, 51: 58-64 (1999).

Rolke et al., "Functional analysis of $H_2O_2$-generating systems in Botrytis cinerea: the major Cu—Zn—superoxide dismutase (BC50D1) contributes to virulence on French bean, whereas a glucose oxidase (BCG0D1) is dispensable," Molecular Plant Pathology, 5(1): 17-27 (2004).

Tsugawa et al., "Fluorescent measurement of 1,5-anhydro-D-glucitol based on a novel marine bacterial glucose dehydrogenase," Enzyme and Microbial Technology, 22: 269-274 (1998).

Yoshida et al., "Construction of multi-chimeric pyrroloquinoline quinone glucose dehydrogenase with improved enzymatic properties and application in glucose monitoring," Biotechnology Letters, 22: 1505-1510 (2000).

Dickinson et al., "The Reactions of 1,10-Phenanthroline with Yeast Alcohol Dehydrogenase," Biochem. J., (1977) 167:237-244.

Pire et al., "NAD(P)+-glucose dehydrogenase from Haloferax mediterranei: kinetic mechanism and metal content," J. Mol. Catalysis B: Enzymatic, 10: 409-417 (2000).

Office Action dated Aug. 18, 2011 in U.S. Appl. No. 12/396,724 (11 pages).

Response to Office Action filed Dec. 16, 2011 in U.S. Appl. No. 12/396,724 (17 pages).

Office Action dated Feb. 14, 2012 in U.S. Appl. No. 12/396,724 (11 pages).

Response to Office Action filed May 11, 2012 in U.S. Appl. No. 12/396,724 (19 pages).

(56) References Cited

OTHER PUBLICATIONS

International Search Report for International Application No. PCT/JP03/16603, dated Mar. 23, 2004 (2 pages).
Matsushita et al., "Membrane-bound D-Glucose Dehydrogenase from *Pseudomonas* sp: Solubilization, Purification and Characterization," Agric. Biol. Chem., 44(7): 1505-1512 (1980).
Ameyama et al., "D-Glucose Dehydrogenase of Gluconobacter suboxydans: Solubilization, Purification and Characterization," Agric. Biol. Chem., 45(4): 851-861 (1981).
Ameyama et al., "Purification of Characterization of the Quinoprotein D-Glucose Dehydrogenase Apoenzyme from *Escherichia coli*," Agric. Biol. Chem., 50(1): 49-57 (1986).
Dokter et al., "The in vivo and in vitro substrate specificity of quinoprotein glucose dehydrogenase of Acinetobacter calcoaceticus LMD 79.41," FEMS Microbiology Letters, 43: 195-200 (1987).
Igarashi et al., "Construction and Characterization of Mutant Water-Soluble PQQ Glucose Dehydrogenases with Altered Km Values—Site-Directed Mutagenesis Studies on the Putative Active Site," Biochemical and Biophysical Research Communications, 264: 820-824 (1999).
Sode et al., "Improved substrate specificity and dynamic range for glucose measurement of *Escherichia coli* PQQ glucose dehydrogenase by site directed mutagenesis," Biotech. Letters, 19(11): 1073-1077 (1997).
Supplementary European Search Report, dated Mar. 23, 2006, in EP Application No. EP 03789625.5 (3 pages).
Oubrie et al., "Active-site structure of the soluble quinoprotein glucose dehydrogenase complexed with methylhydrazine: A covalent cofactor-inhibitor complex," Proceedings of the National Academy of Sciences, 96(21):11787-11791 (1999).
Kotera et al., "Computational Assignment of the EC Numbers for Genomic-Scale Analysis of Enzymatic Reactions," J. Am. Chern. Soc., 126: 16487-16498 (2004).
Jin et al., "Properties of glucoside 3-dehydrogenase and its potential applications, African J. of Biotechnology," 7(25): 4843-4849 (2008).
Creighton, "Proteins Structures and Molecular Properties," Second Edition, W.H. Freeman and Company New York, pp. 260-264 (5 pages).
ISO 15197: In vitro diagnostic test systems—Requirements for blood-glucose monitoring systems for self-testing in managing diabetes mellitus (ISO 15197:2003), International Organization for Standardization, Switzerland 2003 (39 pages).
Bennett et al., "Joslin's Diabetes Mellitus Fourteenth Edition," Chapter 19 "Definition, Diagnosis, and Classification of Diabetes Mellitus and Glucose Homeostasis"; Lippincott Williams & Wilkins, pp. 331-339.
Amiel, "Joslin's Diabetes Mellitus Fourteenth Edition," Chapter 40 "Iatrogenic Hypoglycemia"; Lippincott Williams & Wilkins, pp. 671-686.
Ameyama et al., "Existence of a Novel Prosthetic Group, PQQ, in Membrane-Bound, Electron Transport Chain-Linked, Primary Dehydrogenases of Oxidative Bacteria," FEBS Letters, 130(2): 179-183 (1981).
Cass et al., "Ferrocene-Mediated Enzyme Electrode for Amperometric Determination of Glucose," Am. Chem. Soc., 56(4): 667-671 (1984).
Cozier et al., "Structure of the quinoprotein glucose dehydrogenase of *Escherichia coli* modelled on that of methanol dehydrogenase from Methylobacterium extorquens," Biochem. J., 312: 679-685 (1995).
D'COSTA et al., "Quinoprotein Glucose Dehydrogenase and its Application in an Amperometric Glucose Sensor," Biosensors (1986) 2: 71-87.
FDA—"Avoiding Glucose Monitoring Errors in Patients Receiving Other Sugars (Feb. 2006)," Sep. 2006.
FDA—"Fatal Iatrogenic Hypoglycemia: Falsely Elevated Blood Glucose Readings with a Point-of-Care Meter Due to a Maltose-Containing Intravenous Immune Globulin Product," Jun. 18, 2009.
FDA—"Parenteral Maltose/Parenteral Galactose/Oral Xylose-Containing Products," Apr. 22, 2008.
FDA—"Important Safety Information on Interference With Blood Glucose Measurement Following Use of Parenteral Maltose/Parenteral Galactose/Oral Xylose-Containing Products," May 21, 2009.
"HY-RiSE® Colour Hygiene Test Strip".
"HEMOCUE® Blood Glucose Analyzer Operating Manual".
Lau et al., "Improved specificity of reagentless amperometric PQQ-sGDH glucose biosensors by using indirectly heated electrodes," Biosensors and Bioelectronics, 22: 3014-3020 (2007).
Laurinavičius et al., "A Novel Application of Heterocyclic Compounds for Biosensors Based on NAD, FAD, and PQQ Dependent Oxidoreductases," Monatshefte für Chemie, 130:1269-1281 (1999).
Turner, "Biosensors for process monitoring & control," The World Biotech Report, 1:181-192 (1985).
Wens et al., "A Previously Undescribed Side Effect of Icodextrin: Overestimation of Glycemia by Glucose Analyzer," Peritoneal Dialysis International, 18: 603-609 (1998).
Yoo et al., "Glucose Biosensors: An Overview of Use in Clinical Practice," Sensors, 10: 4558-4576 (2010).
Accession No. Q2USF2, filed in Opposition Proceeding Against EP 2 380 980 (3 pages).
Acuña-Argüelles et al., "Production and properties of three pectinolytic activities produced by Aspergillus niger in submerged and solid-state fermentation," Applied Microbiology and Biotechnology, 43: 808-814 (1995).
Alignment between FAD-linked Glucose Dehydrogenase from Aspergillus terreus (SEQ ID No. 1 from EP2380980 B1) and contig 206 from Aspergillus terreus (cont1.206; Gen Bank accession AAJN01000206.1), submitted to the European Patent Office on Aug. 4, 2015.
Alignment between choline dehydrogenase (GenBank Protein ID BAE55513.1) from Aspergillus oryzae and translated contig 206 from Aspergillus terreus (nt 55816-57706 cont1.206; GenBank accession AAJN01000206.1), submitted to the European Patent Office on Aug. 4, 2015.
Alignment between Glucose Oxidase (GenBank Protein ID EAL93778.1) from Aspergillus fumigatus and translated contig 206 from Aspergillus terreus (nt 55816-57709 cont1.206; GenBank accession AAJN01000206.1), submitted to the European Patent Office on Aug. 4, 2015.
Alignment between the A. fumigatus glucose oxidase and the sequence of SEQ ID No. 2, dated Jul. 27, 2015.
Alignment between the A. oryzae choline dehydrogenase and the sequence of SEQ ID No. 2, dated Jul. 27, 2015.
Alignment between the mutant GLD of A. oryzae and the sequence of SEQ ID No. 2, dated Jul. 31, 2015.
Alignment between the wildtype GLD of A. oryzae and the sequence of SEQ ID No. 2, dated Jul. 31, 2015.
Alignment BLAST of the protein sequence of glucose dehydrogenase of SEQ ID No. 1 and AAJN01000206.1 of Aspergillus terreus NIH2624, GenBank Accession AAJN01000206.1, dated Aug. 4, 2015.
Alignment of sequences of SEQ ID No. 2 and the choline dehydrogenase of A. oryzae and the glucose oxidase of A. fumigatus, submitted to the European Patent Office on Aug. 4, 2015.
Alignment of the protein sequence of glucose dehydrogenase of SEQ ID No. 2 and XM_001216916, dated Jun. 11, 2015.
Alignment of the protein sequence of glucose dehydrogenase SEQ ID No. 2 and European Nucleotide Archive Entry AP007151, dated Dec. 21, 2005.
Amendment after Final filed Mar. 13, 2013, in U.S. Appl. No. 12/866,071 (7 pages).
Amendment and Reply to Final Office Action under 37 C.F.R. § 1.116 filed Apr. 12, 2013 in U.S. Appl. No. 11/886,885 (12 pages).
Amendment and Reply to Restriction Requirement filed Jul. 6, 2012 in U.S. Appl. No. 11/886,885 (16 pages).
Amendment and Response to Restriction Requirement filed Aug. 27, 2012, in U.S. Appl. No. 12/866,071 (7 pages).
Amendment filed Dec. 26, 2012, in U.S. Appl. No. 12/866,071 (15 pages).
Ashcroft, Ion Channels and Disease, Academic Press, San Diego, CA, pp. 54-55 (1999).

(56) References Cited

OTHER PUBLICATIONS

Bak et al., "Studies on the Glucose Dehydrogenase of Aspergillus Oryzae. I. Induction of its synthesis by p-benzoquinone and hydroquinone," Biochim. Biophys. Acta, 139: 265-276 (1967) (7 pages).
BIOspektrum, 10. Jahrgang, Neu auf dem Markt, GlycoProfile—neue Kits für Glycoprotein-Analysen (pp. 218-221) (4 pages).
Cavener, "GMC Oxidoreductases: A Newly Defined Family of Homologous Proteins with Diverse Catalytic Activities," J. Mol. Biol., 223:811-814 (1992).
Cavener, D. et al., "Biphasic expression and function of glucose dehydrogenase in *Drosophila melanogaster*," Proc. Natl. Acad. Sci., 80: 6286-6288 (1983).
Chica et al., "Semi-rational approaches to engineering enzyme activity: combining the benefits of directed evolution and rational design," Current Opinion in Biotechnology, 16: 378-384 (2005).
Communication pursuant to Rule 114(2) EPC issued Aug. 26, 2010 by the European Patent Office in connection with European Patent Application No. 06730146.5 (7 pages).
CV of Takahide Kishimoto, submitted to the European Patent Office on Aug. 4, 2015.
De Baetselier et al., "Fermentation of a Yeast Producing A. Niger Glucose Oxidase: Scale-Up, Purification and Characterization of the Recombinant Enzyme," Nature Biotechnology, 9: 559-561 (1991).
DEAE Cellulofine Ion Exchange Chromatography, Seikagaku Corp. (Mar. 10, 1988) (pp. 1-14) (29 pages in total, including translation).
Declaration of Dr. Kitabayashi, Oct. 7, 2016 (pp. 1-4) (4 pages).
Declaration of Mr. Kawai, Oct. 7, 2016 (5 pages).
Response to Office Action filed Oct. 25, 2017 in U.S. Appl. No. 15/079,002 (3 pages).
Notice of Allowance for U.S. Appl. No. 15/079,002, dated Dec. 22, 2017, Examiner Iqbal H. Chowdhury (8 pages).
Declaration of Mr. Kishimoto, Oct. 8, 2016 (10 pages).
Declaration of Prof. Becker, Oct. 4, 2016 (pp. 1-2) (2 pages).
Declaration of Prof. Nishiya, Oct. 6, 2016 (pp. 1-11) (11 pages).
Edge, "Deglycosylation of Glycoproteins by Trifluoromethanesulphonic Acid," Analytical Biochem., 118: 131-137 (1981).
Edge, "Deglycosylation of glycoproteins with trifluoromethanesulphonic acid: elucidation of molecular structure and function," Biochem. J., 376: 339-350 (2003).
Edman, "A method for the determination of amino acid sequence in peptides," Archives of Biochemistry, 22:475-476 (1949).
European Nucleotide Archive entry AAHF01000001: genome sequence of A. Fumigatus, issued Jun. 2, 2005.
European Nucleotide Archive Entry AP007151: A. oryzae genomic DNA, issued Dec. 21, 2005.
European Patent Office correspondence related to Application No. EP 2 380 980 (EP 11 15 6649.3), dated Oct. 10, 2016, from Dr. Jürgen Meier, European Patent Attorney (pp. 1-58) (58 pages).
European Patent Office correspondence related to Application No. EP 2 380 980 (EP 11 15 6649.3), dated Oct. 10, 2016, from Dr. Raphael Bösl, European Patent Attorney (pp. 1-9) (9 pages).
Experiment Report dated Mar. 1, 2015.
Ferri et al., "Review of glucose oxidases and glucose dehydrogenases: A bird's eye view of glucose sensing enzymes," Journal of Diabetes Science and Technology, 5(5): 1068-1076 (2011).
Final Office Action dated Feb. 13, 2013 in U.S. Appl. No. 11/886,885, (12 pages).
Final Office Action dated Jan. 31, 2013, in U.S. Appl. No. 12/866,071, (5 pages).
Frederick et al., "Glucose oxidase from Aspergillus niger. Cloning, gene sequence, secretion from *Saccharomyces cerevisiae* and kinetic analysis of a yeast-derived enzyme," J. Biol. Chem., 265(7): 3793-3802 (1990).
Frylingou et al., "Aspergillus oryzae FAD-GDH (wt): TFMS deglycosylation and peptide mapping," dated Aug. 3, 2015 (7 pages).
Galagan et al., "Sequencing of Aspergillus nidulans and comparative analysis with A. fumigatus and A. oryzae," Nature, 438: 1105-1115 (2005).

Gomi et al., "Cloning and Nucleotide Sequence of the Acid Protease-encoding Gene (pepA) from Aspergillus oryzae," Biosci. Biotech. Biochem., 57 (7), 1095-1100 (1993).
Harayama et al., "Biochemical characterization of sialoprotein "anti-agglutinin" purified from boar epididymal and seminal plasma," Molecular Reproduction and Development, 55: 96-103 (2000).
Harper's Review of Biochemistry, 20th ed., by Martin et al., 1985, p. 503 (19 pages).
Hata, "Gene expression in solid-state culture of Aspergillus oryzae," Journal of the Agricultural Chemical Society of Japan, 76(8): 715-718 (2002).
Hatzinikolaou et al., "A new glucose oxidase from Aspergillus niger: characterization and regulation studies of enzyme and gene," Appl Microbiol. Biotechnol., 46: 371-381 (1996).
Yurimoto et al., "Heterologous gene expression system by methanol-utilizing yeast," Chemistry & Biology, 38(8): 533-540 (2000).
Inose et al., "Cloning and expression of the gene encoding catalytic subunit of thermostable glucose dehydrogenase from Burkholderia cepacia in *Escherichia coli*," Biochimica et Biophysica Acta, 1645:133-138 (2003).
International Search Report issued for International Application No. PCT/JP2006/306198, dated Apr. 25, 2006.
Isao Ishida and Tamie Ando (ed.), "Laboratory Manual for Gene Expression, Production of useful protein in high expression system," Kodansha Scientific Ltd., pp. 100-129 (1994).
Iwashita et al., "Purification and Characterization of Extracellular and Cell Wall Bound beta-Glucosidases from Aspergillus kawachii," Biosci. Biotechnol. Biochem., 62(10): 1938-1946 (1998).
Jarai et al., "Cloning and characterization of the pepD gene of Aspergillus niger which codes for a subtilisin-like protease," Gene, 139: 51-57 (1994).
Jenkins et al., "Glycosylation of recombinant proteins: problems and prospects," Enzyme Microb. Technol., 16:354-364 (1994).
Kainz, Elke et al., "N-Glycan Modification in Aspergillus Species," Applied and Environmental Microbiology, 74(4): 1076-1086 (2008).
Kataoka et al., "*Escherichia coli* transformant expressing the glucose dehydrogenase gene from Bacillus megaterium as a cofactor regenerator in a chiral alcohol production system," Biosci Biotechnol Biochem (1998), 62(1): 167-169.
Kiso et al., "2.1 Dye Binding Method (Bradford method, CBB method)," Basic Biochemistry Experimentation Method, Minako Ozawa, Tokyo Kagaku Dojin Co., Ltd., pp. 3-25, 142-149, and 160-161 (2001).
Kojima et al., "Shinki Glucose Dehydrogenase o Mochiita Sanso Fukan' no-sei Ketto Sensor no Kiso Kento (1)," The Japan Society for Analytical Chemistry Nenkai Koen Yoshishu, 53: 80 (2004).
Kriechbaum et al., "Cloning and DNA sequence analysis of the glucose oxidase gene from Aspergillus niger NRRL-3," FEBS, 255: 63-66 (1989).
Lorenzo et al., "O-glycans as a source of cross-reactivity in determinations of human serum antibodies to Anisakis simplex antigens," Clinical and Experimental Allergy, 30: 551-559 (2000).
Machida et al., "Genome sequencing and analysis of Aspergillus oryzae," Nature, 438: 1157-1161 (2005).
Machida, "EST Analysis of Aspergillus oryzae," Chemistry and Organism, 39: 384-388 (2001).
Maley et al., "Characterization of Glycoproteins and Their Associated Oligosaccharides through the Use of Endoglycosidases," Analytical Biochemistry, 180: 195-204 (1989).
Meier, "Amino acid composition and N-terminal sequencing of Aspergillus oryzae FAD-GDH," submitted to the European Patent Office on Aug. 5, 2015.
Nakayama, "Cell Engineering, separate vol. Visible Experiment Notebook Series, I Illustrated Biological Experiment /No. 3 PCR for reliable amplification," Chihiro Mizutani, Shujunsha Co., Ltd. (1996).
NCBI entry AAJN00000000.1: genome sequence of Aspergillus terreus, dated Jul. 31, 2015.
NCBI entry XM_001216916: Aspergillus terreus NIH2624 hypothetical protein (ATEG_08295), dated Mar. 31, 2008.
NCMI entry XP_002372599: sequence of the glucose oxidase of A. flavus, submitted Jun. 16, 2005.

(56) References Cited

OTHER PUBLICATIONS

New Biochemical Experiment Course 1 Protein II "Primary Structure", Tokyo Kagaku Dojin, Dec. 1, 1993, 1st edition, 2nd printing, pp. 1-24.
New England BioLabs, Inc., 2002-03 Catalog & Technical Reference, pp. 176-177.
News of the BROAD institute of Sep. 30, 2005 regarding the Aspergillus terreus assembly release.
Nielsen et al., "Identification of prokaryotic and eukaryotic signal peptides and prediction of their cleavage sites," Protein Engineering, 10(1): 1-6 (1997).
Nierman et al., "Genomic sequence of the pathogenic and allergenic filamentous fungus Aspergillus fumigatus," Nature, 438: 1151-1156 (2005).
Notice of Allowance for U.S. Appl. No. 11/886,885, dated Nov. 21, 2013, (17 pages).
Notice of Allowance for U.S. Appl. No. 12/866,071, dated Mar. 25, 2013, (6 pages).
Notice of Allowance for U.S. Appl. No. 13/920,445, dated Apr. 7, 2014, (12 pages).
Notice of Allowance for U.S. Appl. No. 13/920,445, dated Jul. 10, 2014, (8 pages).
Notice of Allowance for U.S. Appl. No. 14/184,573, dated Aug. 28, 2015, (10 pages).
Notice of Allowance for U.S. Appl. No. 14/184,573, dated Dec. 23, 2015, (10 pages).
Notice of Allowance for U.S. Appl. No. 14/510,076, dated Sep. 2, 2015, (5 pages).
Notice of Allowance for U.S. Appl. No. 14/510,076, dated Jan. 21, 2016, (7 pages).
Notice of Allowance dated Jan. 23, 2017, in U.S. Appl. No. 15/135,375, (7 pages).
Notice of opposition to a European Patent for EP Patent No. 2380980, dated Aug. 5, 2015, filed by Roche Diabetes Care GmbH (pp. 1-18).
Notice of opposition to a European Patent for EP Patent No. 2380980, dated Aug. 4, 2015, filed by Toyobo, Co., Ltd. (pp. 1-45).
Notice of Submission of Published Documents issued on February 10, 2009 for counterpart Japanese Patent Application No. 2007-509374.
Notification of Reasons for Refusal dated Aug. 9, 2016, in Patent Application No. 2015-154989 Machine Translation.
Office Action dated Aug. 2, 2011 in connection with Japanese Patent Application No. JP 2007-509374.
Office Action dated Apr. 9, 2012 in U.S. Appl. No. 11/886,885, (8 pages).
Office Action dated Aug. 9, 2016, in U.S. Appl. No. 15/135,375, (15 pages).
Office Action dated Jul. 25, 2012, in U.S. Appl. No. 12/866,071, (5 pages).
Office Action dated Jul. 26, 2017 in U.S. Appl. No. 15/496,935 (8 pages).
Office Action dated Nov. 15, 2017 in U.S. Appl. No. 15/496,935 (4 pages).
Office Action dated Sep. 13, 2012 in U.S. Appl. No. 11/886,885, (16 pages).
Office Action dated Sep. 25, 2012, in U.S. Appl. No. 12/866,071, (11 pages).
Okumura et al., "A novel phosolipase $A_2$ inhibitor with leucine-rich repeats from the blood plasma of Agkistrodon blomhoffii siniticus," J. Biol. Chem., 273:19469-19475 (1998).
Okumura et al., "Consideration regarding reaction characteristics of FAD-dependent glucose dehydrogenase with mediator," Review of Polarography, 51(3): 193 (2005) (5 pages).
Package insert of "N-Glycosidase F, recombinant, Peptide-N-glycosidase F, PNGase, F, peptide-$N^4$-(acetyl-β-glucosaminyl) asparagine amidase cloned from Flavobacterium meningosepticum and expressed in E. coli," EC 3.2.218; 3.5.1.52, (Roche), Version 3, May 2003 (2 pages).

Pandey et al., "Solid state fermentation for production of industrial enzymes," Current Science, 77: 149-162 (1999).
Pharmaceutical and Food Safety Bureau Issue No. 0207005, Feb. 7, 2005; "Safety Measures of Simple Instrument for Self-Checking Blood Glucose and Glucose Kit For Self-Testing Blood Glucose (Using Pyrrolo-Quinoline Quinone as Coenzyme in Glucose Dehydrogenase Method)."
PRNewswire of Mar. 4, 2004, Sigma Introduces GlycoProfile™ Kits for Glycoprotein Analysis (pp. 1-4) (4 pages).
Ramesh et al., "Cloning and characterization of the cDNAs and genes (mep20) encoding homologous metalloproteinases from Aspergillus flavus and A. fumigatus," Gene, 165: 121-125 (1995).
Response to Office Action filed Dec. 9, 2016, in U.S. Appl. No. 15/135,375 (9 pages).
Response to Office Action filed Oct. 25, 2017 in U.S. Appl. No. 15/496,935 (5 pages).
Reply to Office Action under 37 C.F.R. § 1.111 filed Dec. 11, 2012 in U.S. Appl. No. 11/886,885 (18 pages).
Revision History of NCBI entry AAJN00000000.1, dated Jul. 29, 2015.
Roche Applied Science, Instruments and Biochemicals, 2005 Catalog, pp. 530-541 (2005).
Romanos et al., "Foreign gene expression in yeast: a review," Yeast, 8: 423-488 (1992).
Sandhya et al., "Comparative evaluation of neutral protease production by Aspergillus oryzae in submerged and solid-state fermentation," Process Biochemistry, 40: 2689-2694 (2005).
Sangadala et al., "Subunit structure of deglycosylated human and swine trachea and Cowper's gland mucin glycoproteins," Molecular and Cellular Biochemistry, 102: 71-93 (1991).
Sen et al., "Developments in Directed Evolution for Improving Enzyme Functions," Applied Biochemistry and Biotechnology, 143(3): 212-223 (2007).
Sigma-Aldrich Press Release, Kits for Glycoprotein Analysis (Mar. 2, 2004) (pp. 1-3) (3 pages), available at http://laboratorytalk.com/article/53744/kits-for-glycoprotein-analysis.
Sode et al., "A novel thermostable glucose dehydrogenase varying temperature properties by altering its quarternary structures," Enzyme and Microbial Technology, 19: 82-85 (1996).
Sojar, Hakimuddin T. et al., "Chemical Deglycosylation of Glycoproteins," Methods in Enzymology, 138: 341-350 (1987).
Spiro, "Protein glycosylation: nature, distribution, enzymatic formation, and disease implications of glycopeptide bonds," Glycobiology, 12(4): 43R-56R (2002).
Stanbury et al., "Principles of Fermentation Technology," Pergamon Press Ltd. 1987 (pp. 3-5, 86-87, 108, 112-115, 145, 196-198, 213-215).
Sumantha et al., "Microbiology and Industrial Biotechnology of Food-Grade Proteases: A Perspective," Food Technol. Biotechnol., 44(2): 211-220 (2006).
Summary of the Annual Meeting of Japan Society for Bioscience 2004, Biotechnology and Agrochemistry, , 96: 2A25p11 (Mar. 5, 2004) (3 pages).
Tsugawa et al., "Purification of a Marine Bacterial Glucose Dehydrogenase from Cytophaga marinoflava and its Application for Measurement of 1,5-Anhydro-D-Glucitol," Applied Biochemistry and Biotechnology, 56:301-310 (1996).
Tsujimura et al., "Novel FAD-Dependent Glucose Dehydrogenase for a Dioxygen-Insensitive Glucose Biosensor," Biosci. Biotechnol. Biochem., 70(3): 654-659 (2006).
Tsujimura et al., "Absolute quantification of glucose by coulometry using novel glucose dehydrogenase," Abstract of the 72nd Meeting of the Electrochemical Society of Japan, 2D04 (2005).
Tsujita et al., "Chemical Properties of the Polysaccharides Associated with Acid Protease of Aspergillus oryzae Grown on Solid Bran Media," J. Biochem., 81: 1063-1070 (1977).
Tsujita et al., "Purification and Characterization of the Two Molecular Forms of Aspergillus oryzae acid protease," Biochimica et Biophysica Acta, 445: 194-204 (1976).
Tsujita et al., "Purification and Characterization of the Two Molecular Forms of Membrane Acid Protease from Aspergillus oryzae," European Journal of Biochemistry, 84: 347-353 (1978).

(56) References Cited

OTHER PUBLICATIONS

Tsujita et al., "Extracellular Acid Protease of Aspergillus oryzae Grown on Liquid Media: Multiple Forms due to Association with Heterogeneous Polysaccharides," J. Bacteriol., 130: 48-56 (1977).
Volc et al., "Pyranose 2-dehydrogenase, a novel sugar oxidoreductase from the basidiomycete fungus Agricus bisporus," Arch Microbial, 167: 119-125 (1997).
Volc et al., "Screening of basidiomycete fungi for the quinone-dependent sugar C-2/C-3 oxidoreductase, pyranose dehydrogenase, and properties of the enzyme from Macrolepiota rhacodes," Arch Microbial 176: 178-186 (2001).
Whittington et al., "Expression of the Aspergillus niger glucose oxidase gene in A. niger, A. nidulans and *Saccharomyces cerevisiae*," Current Genetics, 18: 531-536 (1990).
Witt et al., "Structural and Kinetic Properties of Nonglycosylated Recombinant Penicillium amagasakiense Glucose Oxidase Expressed in *Escherichia coli*," Applied and Environmental Microbiology, 64:1405-1411 (1998).
Yamada et al., "dffA Gene from Aspergillus oryzae encodes L-ornithine $N^5$-oxygenase and is indispensable for deferriferrichrysin biosynthesis," Journal of Bioscience and Bioengineering, 95(1): 82-88 (2003).
Yamada et al., "Transformation System for Aspergillus oryzae with Double Auxotrophic Mutations, niaD and sC," Biosci. Biotech. Biochem., 61(8): 1367-1369 (1997).
Yang et al., "Efficient expression, purification, and characterization of a novel FAD-dependent glucose dehydrogenase from Aspergillus terreus in Pichia pastoris," J. Microbiol. Biotechnol., 24(11): 1516-1524 (2014).
Yang et al., "Expression, characterization and mutagenesis of an FAD-dependent glucose dehydrogenase from Aspergillus terreus," Enzyme and Microbial Technology, 68: 43-49 (2015).
Yoshino et al., "Cloning and expression of catalytic subunit of glucose dehydrogenase from Burkholderia cepacia," Society for Biotechnology, Japan (Oct. 28-30, 2002).
Zámocký et al., "Ancestral gene fusion in cellobiose dehydrogenases reflects a specific evolution of GMC oxidoreductases in fungi," Gene, 338:1-14 (2004).
Office Action dated Nov. 4, 2016 in U.S. Appl. No. 14/951,457, (8 pages).
Office Action dated Aug. 2, 2017 in U.S. Appl. No. 15/079,002, (10 pages).
Office Action dated Dec. 10, 2007 in U.S. Appl. No. 10/540,025 (5 pages).
Response to Office Action filed Feb. 8, 2008 in U.S. Appl. No. 10/540,025 (1 page).
Office Action dated May 22, 2008 in U.S. Appl. No. 10/540,025 (17 pages).
Response to Office Action filed Aug. 22, 2008 in U.S. Appl. No. 10/540,025 (12 pages).
Notice of Allowance dated Dec. 15, 2008 in U.S. Appl. No. 10/540,025 (8 pages).
Matsumoto et al., "Development of a micro-planar Ag/AgCl quasi-reference electrode with long-term stability for an amperometric glucose sensor," Analytic. Chimica Acta, 462: 253-259 (2002).
Office Action dated Feb. 14, 2013 in U.S. Appl. No. 12/396,724 (13 pages).
Response to Office Action filed Jan. 10, 2014 in U.S. Appl. No. 12/396,724 (9 pages).
Office Action dated Feb. 27, 2014 in U.S. Appl. No. 12/396,724 (12 pages).
Office Action dated Feb. 14, 2012 in U.S. Appl. No. 12/851,668 (7 pages).
Response to Office Action filed May 11, 2012 in U.S. Appl. No. 12/851,668 (10 pages).
Office Action dated Jul. 11, 2012 in U.S. Appl. No. 12/851,668 (9 pages).
Response to Office Action filed Oct. 5, 2012 in U.S. Appl. No. 12/851,668 (10 pages).
Advisory Action dated Oct. 16, 2012 in U.S. Appl. No. 12/851,668 (3 pages).
Response to Office Action filed May 28, 2013 in U.S. Appl. No. 12/851,668 (11 pages).
Office Action dated Jul. 2, 2013 in U.S. Appl. No. 12/851,668 (12 pages).
Declaration of A. Turner filed Dec. 27, 2013 in U.S. Appl. No. 12/851,668, with exhibits (175 pages).
Response to Office Action filed Dec. 27, 2013 in U.S. Appl. No. 12/851,668 (17 pages).
Advisory Action dated Jan. 10, 2014 in U.S. Appl. No. 12/851,668 (4 pages).
Appeal Brief filed Jul. 11, 2014 in U.S. Appl. No. 12/851,668 (40 pages).
Examiner's Answer dated Oct. 2, 2014 in U.S. Appl. No. 12/851,668 (24 pages).
Reply Brief filed Dec. 1, 2014 in U.S. Appl. No. 12/851,668 (31 pages).
Decision on Appeal dated Jul. 28, 2017 in U.S. Appl. No. 12/851,668 (17 pages).
Opening Brief filed Feb. 7, 2018 in U.S. Appl. No. 12/851,668, before Court of Appeals for the Federal Circuit (86 pages).
Response Brief filed Apr. 18, 2018 in U.S. Appl. No. 12/851,668, before Court of Appeals for the Federal Circuit (42 pages).
Reply Brief filed Jun. 1, 2018 in U.S. Appl. No. 12/851,668, before Court of Appeals for the Federal Circuit (32 pages).
Advisory Action dated May 8, 2013 in U.S. Appl. No. 11/886,885 (3 pages).
Response to Office Action filed Feb. 2, 2017 in U.S. Appl. No. 14/951,457 (6 pages).
Office Action dated Mar. 23, 2017 in U.S. Appl. No. 14/951,457 (13 pages).
Office Action dated Mar. 1, 2017 in U.S. Appl. No. 15/079,002 (6 pages).
Response to Office Action filed May 16, 2017 in U.S. Appl. No. 15/079,002 (4 pages).
Response to Office Action filed Jul. 7, 2017 in U.S. Appl. No. 15/496,935 (3 pages).
Response to Office Action filed Dec. 22, 2017 in U.S. Appl. No. 15/496,935 (4 pages).
Notice of Allowance dated Jan. 19, 2018 in U.S. Appl. No. 15/496,935 (7 pages).
International Search Report for International Application No. PCT/JP00/02322, dated May 16, 2000 (2 pages).
International Search Report for International Application No. PCT/EP01/12148, dated Mar. 25, 2002 (3 pages).
International Search Report issued for International Application No. PCT/JP00/02872, dated Aug. 8, 2000 (1 page).
Notice of Appeal filed Aug. 26, 2014 in U.S. Appl. No. 12/396,724 (2 pages).
Notice of Appeal Filed Sep. 26, 2017, in U.S. Appl. No. 12/851,668, before the Court of Appeals for the Federal Circuit (20 pages).
Zhang et al., "Purification and characterization of the glucoside 3-dehydrogenase produced by a newly isolated Stenotrophomonas maltrophilia CCTCC M 204024," Appl. Microbio. Biotech., 71: 638-645 (2006).
Office Action dated Mar. 23, 2017 in U.S. Appl. No. 14/951,457 (14 pages).
Office Action dated May 10, 2017 in U.S. Appl. No. 15/496,935 (6 pages).
Notice of Appeal filed Dec. 10, 2012 in U.S. Appl. No. 12/851,668 (2 pages).
Interview Summary dated Jun. 28, 2013 in U.S. Appl. No. 12/851,668 (4 pages).
Notice of Appeal filed Dec. 31, 2013 in U.S. Appl. No. 12/851,668 (1 page).
Decision on Appeal mailed Jul. 28, 2017 in U.S. Appl. No. 12/851,668 (17 pages).
Kishimoto, Experiment Report, filed in Opposition Proceeding Against EP 2 380 980, dated Mar. 1, 2015 (1 page).
GENETYX: Amino Acid Sequence Homology Data Comparing A. oryzae Wild Type Sequence, filed in Opposition Proceeding Against EP 2 380 980, dated Jul. 31, 2015 (1 page).

(56) References Cited

OTHER PUBLICATIONS

GENETYX: Amino Acid Sequence Homology Data Comparing A. oryzae Mutant Sequence, filed in Opposition Proceeding Against EP 2 380 980, dated Jul. 31, 2015 (1 page).
CV of T. Kishimoto, filed in Opposition Proceeding Against EP 2 380 980 (2 pages).
Declaration of K. Gomi, filed in Opposition Proceeding Against EP 2 380 980, dated Mar. 10, 2016 (5 pages).
Declaration of T. Yada, filed in Opposition Proceeding Against EP 2 380 980, dated Mar. 18, 2016 (9 pages).
UniProtKB Results, filed in Opposition Proceeding Against EP 2 380 980, dated Feb. 24, 2016 (5 pages).
Annex: Sequence Comparison of Different FAD-linked Glucose Dehydrogenases (GLDs), filed in Opposition Proceeding Against EP 2 380 980, dated Mar. 11, 2016 (20 pages).
Annex: Comparison of GLDs (Parallel Editor by GENETYX), filed in Opposition Proceeding Against EP 2 380 980 (3 pages).
Annex: Sequence Alignment of SEQ ID No. 2 with PQQ Glucose Dehydrogenase, filed in Opposition Proceeding Against EP 2 380 980, dated Mar. 15, 2016 (3 pages).
Submission to the European Patent Office Concerning Name Change of Toyobo Co., Ltd., filed in Opposition Proceeding Against EP 2 380 980, dated Oct. 23, 2012 (15 pages).
Translation of Submission to the Japan Patent Office, filed in Opposition Proceeding Against EP 2 380 980 (14 pages).
Declaration of M. Ohta, filed in Opposition Proceeding Against EP 2 380 980, dated Mar. 1, 2016 (5 pages).
BLAST and "GeneDoc" Sequence Comparison of A. terreus and B. cepacia GLD, filed in Opposition Proceeding Against EP 2 380 980 (3 pages).
Submission to the European Patent Office Concerning EP Application No. 07739741.2, filed in Opposition Proceeding Against EP 2 380 980, dated Feb. 23, 2010 (2 pages).
Examination Report Concerning EP Application No. 07 739 741. 2-2406, filed in Opposition Proceeding Against EP 2 380 980, dated Oct. 16, 2009 (3 pages).
Shotgun Assembly Sequences: Genome (WGS) and Transcriptome (TSA); AAJN00000000.1 A. terreus NIH2624, filed in Opposition Proceeding Against EP 2 380 980, dated Feb. 14, 2016 (5 pages).
Submission to the European Patent Office Concerning EP Patent Application No. 07739741.2, filed in Opposition Proceeding Against EP 2 380 980, dated Oct. 14, 2010 (3 pages).
General Information for Authors of Food Technology and Biotechnology, filed in Opposition Proceeding Against EP 2 380 980 (1 page).
CV of A. Kawai, filed in Opposition Proceeding Against EP 2 380 980 (1 page).
CV of T. Kishimoto, filed in Opposition Proceeding Against EP 2 380 980 (1 page).
CV of Y. Nishiya, filed in Opposition Proceeding Against EP 2 380 980 (2 pages).
CV of M. Kitabayashi, filed in Opposition Proceeding Against EP 2 380 980 (1 page).
BLAST® (Basic Local Alignment Search Tool), filed in Opposition Proceeding Against EP 2 380 980, dated May 23, 2017 (4 pages).
FASTA Sequence Comparison at the University of Virginia, filed in Opposition Proceeding Against EP 2 380 980, dated May 23, 2017 (1 page).
Notice of Furnishing for Accession No. FERM BP-08578, filed in Opposition Proceeding Against EP 2 380 980, dated May 18, 2016 (1 page).
Declaration of T. Yada, filed in Opposition Proceeding Against EP 2 380 980, dated Jun. 27, 2017 (12 pages).
Declaration of K. Gomi, filed in Opposition Proceeding Against EP 2 380 980, dated Sep. 25, 2017 (6 pages).
Declaration of M. Ohta, filed in Opposition Proceeding Against EP 2 380 980, dated Sep. 22, 2017 (4 pages).
Comparison of Sample from EP 2 380 980, filed in Opposition Proceeding Against EP 2 380 980, dated Sep. 29, 2017 (1 page).
Hata et al., "Comparison of Two Glucoamylases Produced by Aspergillus oryzae in Solid-State Culture (Koji) and in Submerged Culture," J. Fermentation & Bioeng., 84(6): 532-537 (1997).
Ishida et al., Isolation of a Novel Promoter for Efficient Protein Production in Aspergillus oryzae, Bioscience Biotechnology Biochemistry, 68(9): 1849-1857 (2004).
Revision History of Accession No. XP_002372599.1, filed in Opposition Proceeding Against EP 2 380 980, dated Sep. 29, 2017 (1 page).
Annex: Sequence Comparison of Different FAD-linked Glucose Dehydrogenases (GLDs) (Updated), filed in Opposition Proceeding Against EP 2 380 980 (27 pages).
GENETYX: Homology Data, filed in Opposition Proceeding Against EP 2 380 980, dated May 17, 2017 (1 page).
Markel et al., "Sequence Analysis in a Nutshell: A Guide to Common Tools and Databases," O'Reilly & Associates, Inc., pp. 158-159 (2003).
EMBOSS Pairwise Alignment Algorithms, filed in Opposition Proceeding Against EP 2 380 980, dated Mar. 17, 2005 (1 of 2) (1 page).
EMBOSS Pairwise Alignment Algorithms, filed in Opposition Proceeding Against EP 2 380 980, dated Mar. 17, 2005 (2 of 2) (1 page).
Shin Nihon Chemical Co., Ltd., Sumizyme PX Umizyme, filed in Opposition Proceeding Against EP 2 380 980 (2 pages).
Shin Nihon Chemical Co., Ltd., Sumizyme ARS Umizyme, filed in Opposition Proceeding Against EP 2 380 980 (2 pages).
Declaration of M. Ohta, filed in Opposition Proceeding Against EP 2 380 980, dated Oct. 12, 2018 (3 pages).
Declaration of G. Pasut, filed in Opposition Proceeding Against EP 2 380 980, dated Oct. 16, 2018 (12 pages).
Glick, Methods of Biochemical Analysis vol. III, pp. v-vii, 111-152.
Thermo Scientific, Instructions for GlycoLink™ Coupling Catalyst, filed in Opposition Proceeding Against EP 2 380 980 (4 pages).
Sigma, Sodium Borohydride Product Information, filed in Opposition Proceeding Against EP 2 380 980 (1 page) (D120c).
European Patent Office Opposition Decision, filed in Opposition Proceeding Against EP 2 380 980, dated Jan. 25, 2018 (37 pages).
European Patent Office Summary of Proceedings and Submitted Evidence, filed in Opposition Proceeding Against EP 2 380 980, dated Feb. 16, 2017 (19 pages).
Response by Ikeda Food Research Co., Ltd., filed in Opposition Proceeding Against EP 2 380 980, dated Oct. 17, 2018 (90 pages).
Response by Ikeda Food Research Co., Ltd., filed in Opposition Proceeding Against EP 2 380 980, dated Mar. 21, 2016 (84 pages).
Response by Ikeda Food Research Co., Ltd., filed in Opposition Proceeding Against EP 2 380 980, dated Sep. 29, 2017 (44 pages).
Grounds of Appeal by Roche Diabetes Care GmbH, filed in Opposition Proceeding Against EP 2 380 980, dated Jun. 4, 2018 (21 pages).
Response by Roche Diabetes Care GmbH, filed in Opposition Proceeding Against EP 2 380 980, dated Sep. 29, 2017 (10 pages).
Grounds of Appeal by Toyobo Co., Ltd., filed in Opposition Proceeding Against EP 2 380 980, dated Jan. 25, 2018 (45 pages).
Response by Toyobo Co., Ltd., filed in Opposition Proceeding Against EP 2 380 980, dated Nov. 29, 2017 (10 pages).
Office Action in EP Application No. 11 156 649.3, dated Apr. 12, 2013 (4 pages).
Office Action in EP Application No. 11 156 649.3, dated May 31, 2012 (4 pages).
Office Action in EP Application No. 11 156 649.3, dated Aug. 12, 2013 (4 pages).
Office Action in EP Application No. 11 156 649.3, dated Nov. 28, 2012 (4 pages).
Response to Office Action in EP Application No. 11 156 649.3, dated Feb. 11, 2013 (6 pages).
Response to Office Action in EP Application No. 11 156 649.3, dated Apr. 26, 2012 (9 pages).
Response to Office Action in EP Application No. 11 156 649.3, dated Jul. 30, 2013 (25 pages).
Response to Office Action in EP Application No. 11 156 649.3, dated Oct. 16, 2013 (9 pages).

(56) References Cited

OTHER PUBLICATIONS

Response to Office Action in EP Application No. 11 156 649.3, dated Oct. 31, 2012 (13 pages).
Pairwise Sequence Alignment, filed in Opposition Proceeding Against EP 2 380 980, dated May 23, 2017 (3 pages).
FAD-dependent Glucose Dehydrogenase [R. emersonii], GenBank No. BAV89805.1, filed in Opposition Proceeding Against EP 2 380 980, dated Jul. 7, 2017 (1 page).
EMBOSS Needle—Alignment, filed in Opposition Proceeding Against EP 2 380 980, dated Sep. 21, 2017 (1 of 2) (3 pages).
EMBOSS Needle—Alignment, filed in Opposition Proceeding Against EP 2 380 980, dated Sep. 21, 2017 (2 of 2) (3 pages).
SEQ ID Nos. 9 and 10, filed in Opposition Proceeding Against EP 2 380 980 (2 pages).
FASTA Query Results, filed in Opposition Proceeding Against EP 2 380 980, dated Sep. 21, 2017 (1 page).
Christensen et al., "High Level Expression of Recombinant Genes in Aspergillus oryzae," Nature Biotechnology, 6:1419-1422 (1988).
Hannig et al., "Strategies for optimizing heterologous protein expression in *Escherichia coli*," TIBTECH, 16:54-60 (1998).
Heilmann et al., "Identification and isolation of glucose dehydrogenase genes of Bacillus megaterium M1286 and their expression in *Escherichia coli*," Eur. J. Biochem., 174:485-490 (1988).
Markwell et al., "Aspergillus niger mutants with increased glucose oxidase production," Appl. Microbial. Biotechnol., 30:166-169 (1989).
Office Action in U.S. Appl. No. 16/145,106, dated Jan. 3, 2019 (36 pages).
Office Action in U.S. Appl. No. 16/145,132, dated Jan. 2, 2019 (31 pages).
Office Action in U.S. Appl. No. 16/145,146, dated Jan. 3, 2019 (31 pages).
Office Action in U.S. Appl. No. 16/145,152, dated Jan. 2, 2019 (36 pages).
Office Action in U.S. Appl. No. 16/145,165, dated Jan. 2, 2019 (31 pages).
Office Action in U.S. Appl. No. 16/145,166, dated Jan. 2, 2019 (36 pages).
Office Action in U.S. Appl. No. 16/145,170, dated Jan. 2, 2019 (35 pages).
Office Action in U.S. Appl. No. 16/145,174, dated Jan. 2, 2019 (32 pages).
Office Action in U.S. Appl. No. 16/145,178, dated Jan. 2, 2019 (31 pages).
Office Action in U.S. Appl. No. 16/145,184, dated Jan. 7, 2019 (35 pages).
Office Action in U.S. Appl. No. 16/145,190, dated Jan. 2, 2019 (31 pages).
Office Action in U.S. Appl. No. 16/145,191, dated Jan. 3, 2019 (30 pages).
Record of Oral Hearing in U.S. Appl. No. 12/851,668, mailed Jun. 20, 2017 (15 pages).
Federal Circuit Opinion in U.S. Appl. No. 12/851,668, issued Jan. 29, 2019 (16 pages).
Petition for Post Grant Review in PGR2019-00031, Patent No. 9,957,543, with Exhibits 1001 to 1019, filed Jan. 30, 2019 (840 pages).
Petition for Post Grant Review in PGR2019-00032, Patent No. 9,976,125, with Exhibits 1001 to 1028, filed Jan. 30, 2019 (1454 pages).
Merry et al., "Chemical and Enzymatic Release of Glycans from Glycoproteins," Methods in Molecular Biology, 213:27-40 (2003).
Definition of "Eluates" from the Free Dictionary, filed in Opposition Proceeding Against EP 2 380 980, dated Feb. 28, 2019 (1 page).
Declaration of Y. Nishiya, filed in Opposition Proceeding Against EP 2 380 980, dated Feb. 26, 2019 (2 pages).
Declaration of U. Kinkeldey, filed in Opposition Proceeding Against EP 2 380 980, dated Mar. 1, 2019 (11 pages).
Definition of "Encompass," filed in Opposition Proceeding Against EP 2 380 980, undated (1 page).
Opposition by Toyobo Co., Ltd., filed in Opposition Proceeding Against EP 2 380 980, dated Mar. 5, 2019 (11 pages).
Letter by W. Hörschler, filed in Opposition Proceeding Against EP 2 380 980, dated Dec. 21, 2018 (1 page).
Office Action in Japanese Appl. No. 2017-242354, dated Dec. 11, 2019 (4 pages).
Office Action in U.S. Appl. No. 15/955,650, dated Feb. 8, 2019 (6 pages).
Alignment to U.S. Pat. No. 7,553,649; SEQ ID No. 4; Jul. 2012.
Alignment to U.S. Pat. No. 7,553,649; SEQ ID No. 5; Sep. 2012.
Amendment and Response to Office Action filed Apr. 1, 2019 in U.S. Appl. No. 16/145,170 (11 pages).
Amendment and Response to Office Action filed Apr. 1, 2019 in U.S. Appl. No. 16/145,174 (11 pages).
Amendment and Response to Office Action filed Mar. 7, 2019 in U.S. Appl. No. 16/145,178 (10 pages).
Amendment and Response to Office Action filed Mar. 20, 2019 in U.S. Appl. No. 16/145,184 (11 pages).
Amendment and Response to Office Action filed Mar. 7, 2019 in U.S. Appl. No. 16/145,190 (11 pages).
Amendment and Response to Office Action filed Mar. 20, 2019 in U.S. Appl. No. 16/145,191 (11 pages).
Decision to Grant Patent in Japanese Appl. No. JP 2017-242354, dated Apr. 2, 2019 (4 pages).
Office Action in U.S. Appl. No. 16/278,030, dated Apr. 18, 2019 (21 pages).
Office Action in U.S. Appl. No. 16/278,008, dated May 2, 2019 (25 pages).
Office Action in U.S. Appl. No. 16/278,019, dated Apr. 18, 2019 (20 pages).
Office Action in U.S. Appl. No. 16/278,025, dated May 2, 2019 (25 pages).
Amendment and Response to Office Action in U.S. Appl. No. 16/278,030, filed May 23, 2019 (9 pages).
Amendment and Response to Office Action in U.S. Appl. No. 16/278,008, filed May 23, 2019 (9 pages).
Amendment and Response to Office Action in U.S. Appl. No. 16/278,019, filed May 23, 2019 (9 pages).
Amendment and Response to Office Action in U.S. Appl. No. 16/278,025, filed May 23, 2019 (9 pages).
Applicant-Initiated Interview Summary in U.S. Appl. No. 16/145,178, dated May 2, 2019 (3 pages).
Applicant-Initiated Interview Summary in U.S. Appl. No. 16/145,184, dated May 7, 2019 (4 pages).
Applicant-Initiated Interview Summary in U.S. Appl. No. 16/145,190, dated May 7, 2019 (4 pages).
Applicant-Initiated Interview Summary in U.S. Appl. No. 16/145,191, dated May 2, 2019 (3 pages).
Applicants' Summary of Apr. 24, 2019 Interview in U.S. Appl. No. 16/145,178, filed Apr. 29, 2019 (9 pages).
Applicants' Summary of Apr. 24, 2019 Interview in U.S. Appl. No. 16/145,184, filed Apr. 29, 2019 (9 pages).
Applicants' Summary of Apr. 24, 2019 Interview in U.S. Appl. No. 16/145,190, filed Apr. 29, 2019 (9 pages).
Applicants' Summary of Apr. 24, 2019 Interview in U.S. Appl. No. 16/145,191, filed Apr. 29, 2019 (9 pages).
Patent Owner's Preliminary Response in Case No. PGR2019-00031, filed May 28, 2019 (74 pages).
Patent Owner's Preliminary Response in Case No. PGR2019-00032, filed May 28, 2019 (53 pages).
Office Action in U.S. Appl. No. 16/145,170, dated May 29, 2019 (18 pages).
Office Action in U.S. Appl. No. 16/145,178, dated May 30, 2019 (25 pages).
Office Action in U.S. Appl. No. 16/145,184, dated May 24, 2019 (19 pages).
Office Action in U.S. Appl. No. 16/145,190, dated May 23, 2019 (19 pages).
Office Action in U.S. Appl. No. 16/145,191, dated May 30, 2019 (26 pages).
Response to Office Action in U.S. Appl. No. 16/145,170, filed Jun. 11, 2019 (7 pages).

(56) References Cited

OTHER PUBLICATIONS

Response to Office Action in U.S. Appl. No. 16/145,178, filed Jun. 11, 2019 (6 pages).
Response to Office Action in U.S. Appl. No. 16/145,184, filed Jun. 11, 2019 (6 pages).
Response to Office Action in U.S. Appl. No. 16/145,190, filed Jun. 11, 2019 (6 pages).
Response to Office Action in U.S. Appl. No. 16/145,191, filed Jun. 11, 2019 (6 pages).
Office Action in U.S. Appl. No. 15/927,949, dated Apr. 19, 2019 (6 pages).
Office Action in U.S. Appl. No. 15/927,976, dated May 20, 2019 (6 pages).
Office Action in U.S. Appl. No. 15/928,012, dated May 17, 2019 (6 pages).
Office Action in U.S. Appl. No. 15/928,027, dated Apr. 22, 2019 (6 pages).
Amendment and Response to Office Action in U.S. Appl. No. 15/927,949, filed Jun. 19, 2019 (7 pages).
Amendment and Response to Office Action in U.S. Appl. No. 15/927,976, filed Jun. 19, 2019 (7 pages).
Amendment and Response to Office Action in U.S. Appl. No. 15/928,027, filed Jun. 19, 2019 (7 pages).
Petitioner's Opposition to Revised Motion to Amend Under 37 C.F.R. § 42.221 dated Apr. 30, 2020, Case No. PGR2019-00032, including 13 exhibits, 190 pages.
Non-Final Office Action from U.S. Appl. No. 16/145,196 dated Jun. 25, 2020.
Notice of Allowance from U.S. Appl. No. 15/928,027 dated Jun. 29, 2020.
Final Office Action from U.S. Appl. No. 16/278,030 dated Jul. 8, 2020.
Decision on Petition from U.S. Appl. No. 16/145,178 dated Jul. 9, 2020.
Examiner's Answer from U.S. Appl. No. 16/145,184 dated Jul. 13, 2020.
Examiner's Answer from U.S. Appl. No. 16/145,170 dated Jul. 13, 2020.
Second Examiner's Answer from U.S. Appl. No. 16/278,008 dated Jul. 20, 2020.
Patent Owners' Reply to Petitioner's Opposition to Patent Owners' Revised Motion to Amend Under 37 C.F.R. § 42.221 dated May 21, 2020, Case No. PGR2019-00032, including 4 exhibits, 41 pages.
Petitioner's Surreply to Patent Owners' Reply to Opposition to Revised Motion to Amend Under 37 C.F.R. § 42.221 dated Jun. 11, 2020, Case No. PGR2019-00032, 20 pages.
Record of Oral Hearing dated Jul. 16, 2020, Case No. PGR2019-00032, 40 pages.
Track One Request, RCE, Response to Aug. 16, 2019 Final Office Action, Declaration of Masaaki Kotera Under 37 C.F.R. 1.132, and Supp. IDS filed on Oct. 28, 2019 in U.S. Appl. No. 16/278,030.
Communication in Response to Dec. 26, 2019 Office Action and Supp. IDS filed on Mar. 25, 2020 in U.S. Appl. No. 16/278,030.
Track One Request, RCE, Response to Aug. 14, 2019 Final Office Action, Declaration of Masaaki Kotera Under 37 C.F.R. 1.132, and Supp. IDS filed on Oct. 28, 2019 in U.S. Appl. No. 16/278,008.
Appeal Brief filed on Aug. 14, 2020 in U.S. Appl. No. 16/278,030.
Reply Brief, Certification and Transmittal of Appeal Forwarding Fee, and Request for Oral Hearing filed on Aug. 18, 2020 in U.S. Appl. No. 16/145,170.
Non-Final Office Action from U.S. Appl. No. 15/955,650 dated Oct. 29, 2019.
Non-Final Office Action from U.S. Appl. No. 16/145,174 dated Oct. 31, 2019.
Non-Final Office Action from U.S. Appl. No. 16/278,008 dated Nov. 15, 2019.
Response to Oct. 31, 2019 Office Action filed on Dec. 24, 2019 in U.S. Appl. No. 16/145,174, including Second Declaration of Katsuya Gomi Under 37 CFR 1.132 and six references.
Counterstatement, including five cited documents (D36b, D126, D127, D128, and T0156-3.3.07), filed in European Patent Office on Dec. 6, 2019 relating to Opposition of European Patent No. 2,380,980.
Decision to Grant a Patent dated Aug. 4, 2020 from Japanese Patent Application No. 2019-100865, with English Language machine translation.
Decision—Final Written Decision Granting-in-Part and Denying-in-Part Patent Owners' Motion to Amend 35 U.S.C. § 328 dated Aug. 12, 2020, Case No. PGR2019-00032, 34 pages.
Advisory Action dated Jun. 26, 2019 in U.S. Appl. No. 16/145,170 (9 pages).
Advisory Action dated Jun. 27, 2019 in U.S. Appl. No. 16/145,178 (11 pages).
Advisory Action dated Jun. 27, 2019 in U.S. Appl. No. 16/145,184 (9 pages).
Advisory Action dated Jun. 27, 2019 in U.S. Appl. No. 16/145,191 (12 pages).
Advisory Action dated Jun. 28, 2019 in U.S. Appl. No. 16/145,190 (10 pages).

\* cited by examiner

COENZYME-BINDING GLUCOSE DEHYDROGENASE

TECHNICAL FIELD

The present invention relates to a novel soluble coenzyme-binding glucose dehydrogenase, a method for producing the coenzyme-binding glucose dehydrogenase, and a microorganism having an ability of producing the coenzyme-binding glucose dehydrogenase.

The invention also relates to a method for measuring glucose in a sample employing the coenzyme-binding glucose dehydrogenase, and a reagent and a reagent composition containing the coenzyme-binding glucose dehydrogenase. Moreover, the invention relates to utilization in producing and analyzing a material such as a starting material, including a method for producing an organic compound.

The invention further relates to a biosensor capable of rapidly and conveniently quantifying a particular component in a sample at a high accuracy. Practically, the invention relates to a glucose sensor employing the coenzyme-binding glucose dehydrogenase.

BACKGROUND ART

Glucose is present in blood and utilized as an important marker for diabetes. A method for measuring a glucose has conventionally been a chemical method or an enzymatic method, and an enzymatic method is regarded generally to be excellent in view of the specificity and the safety. Such an enzymatic method is, for example, be a measurement using a glucose oxidase, glucose-6-phosphate dehydrogenase or an NAD(P)-dependent glucose dehydrogenase. However, the methods employing the glucose oxidase and the glucose-6-phosphate dehydrogenase are not convenient reaction systems since they employ a plural of enzymes. The methods employing the glucose-6-phosphate dehydrogenase and the NAD(P)-dependent glucose dehydrogenase pose a complication due to the requirement of adding a coenzyme NAD(P) to the reaction systems.

Recently, various biosensors were proposed as modes for quantifying a particular component in a sample conveniently without diluting or stirring a sample solution. For example, a biosensor was proposed in which an electrode system consisting of an action electrode, a counter electrode and a reference electrode was formed by a screen printing on an insulating board. This electrode system and the like was in contact with an enzymatic reaction layer formed thereon containing a hydrophilic polymer, a redox enzyme and an electron acceptor.

The number of diabetes patient is increasing year by year, and a method for measuring a blood sugar and a means for controlling the blood sugar level are desired which can be utilized not only in a hospital but also at home and which is convenient. While a simple glucose sensor is employed currently for measuring the blood sugar, it frequently employs a glucose oxidase which is highly suspected to give a measured value involving an error due to a level of the residual oxygen. On the other hand, a biosensor employing a glucose dehydrogenase which is dependent on a nicotinamide-based coenzyme exhibits a high background noise and involves a complicated reaction system due to the requirement of adding a coenzyme or an auxiliary enzyme separately, and it also suffers from a disadvantage due to the requirement of an expensive optical system upon measuring a chromogenic system.

As an enzyme which is not affected by the residual oxygen level and which can act on glucose in the absence of NAD(P), a glucose dehydrogenase whose coenzyme is pyrroloquinolinequinone is known, but the pyrroloquinolinequinone problematically tends to dissociate from the enzyme. A glucose dehydrogenase whose coenzyme is pyrroloquinolinequinone disclosed in JP-A-2000-350588 and JP-A-2001-197888 has a disadvantageously low selectivity for glucose. On the other hand, a glucose dehydrogenase whose coenzyme is the pyrroloquinolinequinone derived from *Escherichia coli* (JP-A-10-243786), a glucose dehydrogenase whose coenzyme is the pyrroloquinolinequinone derived from *Pseudomonas* sp. (Agric. Biol. Chem. (1980) 44:1505-1512) and a glucose dehydrogenase whose coenzyme is the pyrroloquinolinequinone derived from *Gluconobacter suboxydans* (Agric. Biol. Chem. (1981) 45:851-861) had the respective activity on maltose of 3%, 3.2% and 5%, but were accompanied with the complication due to the requirement of a solubilization and an extraction of the enzymes since they were existing in a membrane fraction of the bacterial bodies.

The coenzyme-binding glucose dehydrogenases which oxidize a hydroxyl group in the 3rd-position of glucose were also reported in J. Biol. Chem. (1967) 242: 3665-3672, Appl. Microbiol. Biotechnol. (1999) 51: 58-64, Appl. Biochem. Biotechnol. (1996) 56: 301-310 and Enzyme Microb. Technol. (1998) 22:269-274, but any of them exhibits a poor selectivity for glucose. Since maltose is employed widely as an infusion component and the blood maltose level in an infused patient is high, it is desired to develop an enzyme for measuring the blood sugar which is capable of acting specifically on glucose and has low activity especially on maltose.

In order to respond the industrial needs mentioned above, an objective of the invention is to provide a novel glucose dehydrogenase which exhibits an excellent substrate-recognizing ability toward glucose and which has low activity on maltose, and also to provide a method for producing the same and a microorganism having an ability of producing the same.

Another objective of the invention is to provide excellent glucose measuring method, measuring reagent and biosensor which employ the novel glucose dehydrogenase and which are capable of quantifying glucose rapidly and conveniently at a high accuracy, as well as a glucose-eliminating reagent.

DISCLOSURE OF THE INVENTION

The invention is accomplished for solving the problems mentioned above, and the inventors made an effort in various ways and then focused on a novel soluble coenzyme-binding glucose dehydrogenase. The coenzyme-binding glucose dehydrogenase catalyzes a glucose-oxidizing reaction in the presence of an electron acceptor, and is classified for example as EC (Enzyme Code) 1.1.99. The inventors also made an effort in characterizing various microorganisms producing the coenzyme-binding glucose dehydrogenase, and finally discovered a coenzyme-binding glucose dehydrogenase-producing microorganism and a coenzyme-binding glucose dehydrogenase.

The invention provides a glucose dehydrogenase to which a coenzyme is bound continuously upon a catalytic reaction. The coenzyme-binding glucose dehydrogenase has a physicochemical ability of catalyzing a reaction for oxidizing glucose, especially a hydroxyl group in the 1st-position of glucose, in the presence of an electron acceptor. The coenzyme-binding glucose dehydrogenase has 5% or less activity to maltose, preferably 3% or less; thus it has a poor activity on the maltose. On the other hand, the coenzyme-binding glucose dehydrogenase allows its enzymatic activity to be inhibited characteristically by 50% or more at 5 mM of 1,10-phenanthroline, preferably by 50% or more at 2 mM as a final concentration of 1,10-phenanthroline, more preferably by 50% or more at 1 mM of 1,10-phenanthroline. The coenzyme-binding glucose dehydrogenase preserves its residual enzymatic activity at a level as high as 85% or more even after a heat treatment for 15 minutes at 50° C. in the presence of 50 mM sodium citrate buffer solution (pH5.5). The coenzyme which is bound to the inventive glucose dehydrogenase may for example be a flavin compound, including a coenzyme such as flavin adenine dinucleotide. The invention also includes, with respect to a protein having the characteristics of those of the coenzyme-binding glucose dehydrogenase and/or characteristics equivalent substantially thereto as well as its salt, a protein which has an amino acid sequence encoding the protein or an amino acid sequence containing a mutation resulting from a deletion, substitution or addition of one or more amino acid residues in the sequence and which is biologically active and stable. Moreover, the inventive coenzyme-binding glucose dehydrogenase is a microorganism-derived coenzyme-binding glucose dehydrogenase, preferably a eukaryotic microorganism-derived coenzyme-binding glucose dehydrogenase, more preferably the deposited strain FERM BP-08578-derived coenzyme-binding glucose dehydrogenase.

It has already been observed that a glucose dehydrogenase whose coenzyme is a flavin adenine dinucleotide exists in a cytoplasm fraction and a culture of *Aspergillus oryzae* (TCHAN-GI BAK (BIOCHEMICA ET BIOPHYSICA ACTA. (1967) 139:277-293)). However, this glucose dehydrogenase is inhibited only by a heavy metal ion, and characterized physicochemically in that it is not inhibited by a metal chelator including 1,10-phenanthroline. Accordingly, in a measurement system employing this glucose dehydrogenase, only a heavy metal can be used as a quencher, which poses a problem associated with a complicated heavy metal waste disposal after completion of the reaction. In addition, this enzyme has a poor stability, and is problematic when used practically. On the other hand, the coenzyme-binding glucose dehydrogenase discovered in this invention is characterized by its higher stability when compared with that of the known *Aspergillus oryzae*-derived coenzyme-binding glucose dehydrogenase, and also by a favorably convenient handling for quenching because of its ability of being inhibited by a trace amount of 1,10-phenanthroline in addition to a heavy metal ion.

The invention provides a method for producing the novel soluble coenzyme-binding glucose dehydrogenase.

The invention provides a microorganism having an ability of producing the novel soluble coenzyme-binding glucose dehydrogenase.

The microorganism is preferably a eukaryotic microorganism, more preferably, genus *Aspergillus*, further preferably, *Aspergillus terreus*, and most preferably, the deposited strain FERM BP-08578.

The invention provides a method using the novel soluble coenzyme-binding glucose dehydrogenase. Preferably, a method for measuring glucose using the coenzyme-binding glucose dehydrogenase is provided for measuring glucose in a sample. A method for eliminating glucose using the coenzyme-binding glucose dehydrogenase and a method for producing an organic compound are also provided.

The invention provides a reagent containing the novel soluble coenzyme-binding glucose dehydrogenase. The reagent is preferably a glucose-measuring reagent containing the coenzyme-binding glucose dehydrogenase employed for measuring the glucose in a sample, and a glucose-eliminating reagent containing the coenzyme-binding glucose dehydrogenase as well as an organic compound-producing reagent.

The invention provides a reagent composition containing the novel soluble coenzyme-binding glucose dehydrogenase. The composition is preferably a glucose-measuring composition containing the coenzyme-binding glucose dehydrogenase employed for measuring glucose in a sample, and a glucose-eliminating composition containing the coenzyme-binding glucose dehydrogenase as well as an organic compound-producing composition.

The invention provides a biosensor employing the novel soluble coenzyme-binding glucose dehydrogenase and a biosensor capable of quantifying and/or qualifying a particular component in a sample. Such a biosensor is preferably a glucose sensor employing the coenzyme-binding glucose dehydrogenase.

One preferred embodiment of these inventive measurement methods, measurement reagents, measurement compounds and biosensors is characterized by the use of potassium ferricyanide (potassium hexacyanoferrate (III)) at a final concentration of 2 mM to 500 mM.

In the invention, a value of percentage (%) represents "substrate specificity". For example, in the expressions "activity to maltose", "activity" toward maltose" or an analogous expression, according to the coenzyme-binding glucose dehydrogenase, such a value also represents for a percentage of a relative intensity of an enzymatic activity on the maltose or other action targets based on the enzymatic activity on glucose being regarded as 100%.

BEST MODE FOR CARRYING OUT THE INVENTION

Figure 1:
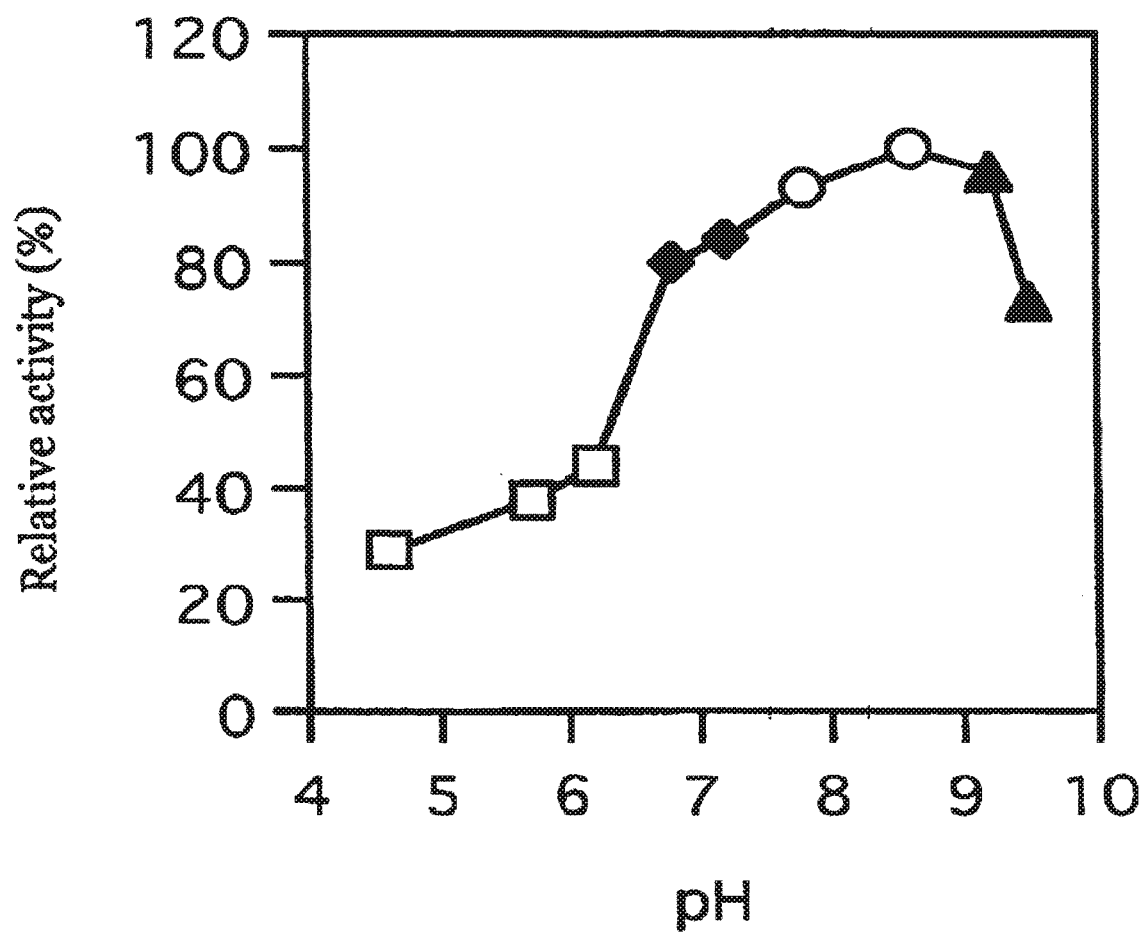
FIG. 1 shows a graph representing the relationship between the relative activity (%) of the coenzyme-binding glucose dehydrogenase and the pH, in Example 3 (3.2). Symbols show measured values and types of buffer solutions, which are □: citric acid-sodium phosphate buffer (pH4.6 to 6.2), ♦: potassium phosphate buffer (pH6.8 to 7.2), ○: Tris-HCl buffer (pH7.8 to 8.6) and ▲: glycine-sodium hydroxide (pH9.2 to 9.5). The optimum pH of the enzyme was 7.0 to 9.0.

An inventive coenzyme-binding glucose dehydrogenase may for example be an enzyme classified as EC 1.1.99, preferably EC 1.1.99.10, EC 1.1.99.13 or EC 1.1.99.17, and is a coenzyme-binding enzyme, preferably a soluble coenzyme-binding enzyme. That is, it is an enzyme capable of being obtained in the state of an aqueous solution without using any surfactant in a step of extraction/purification of the enzyme. As used herein, a coenzyme may be any flavin compound, such as flavin adenine dinucleotide, flavin mononucleotide and the like.

The inventive coenzyme-binding glucose dehydrogenase may be a glucose dehydrogenase to which a coenzyme is bound always over the period of the catalytic reaction. The coenzyme-binding glucose dehydrogenase has at least the following characteristics; that is a physicochemical property for catalyzing a reaction for oxidizing glucose in the presence of an electron acceptor, especially for catalyzing a reaction for oxidizing a hydroxyl group in the 1st-position of the glucose. In addition, the coenzyme-binding glucose dehydrogenase has a low activity on maltose, which is at a level for example of 5% or below, preferably 3% or below. Moreover, the enzymatic activity of the coenzyme-binding glucose dehydrogenase is inhibited by 50% or more at 5 mM of 1,10-phenanthroline, preferably by 50% or more at 2 mM as a final concentration of 1,10-phenanthroline, more preferably by 50% or more at 1 mM of 1,10-phenanthroline, especially by 60% or more at 1 mM of 1,10-phenanthroline. The coenzyme-binding glucose dehydrogenase preserves its residual enzymatic activity at a level as high as 85% or more even after a heat treatment for 15 minutes at 50° C. in the presence of 50 mM sodium citrate buffer solution (pH5.5). Moreover, the invention relates to coenzyme-binding glucose dehydrogenase having the physicochemical characteristics described above; or an amino acid sequence encoding the physicochemical characteristics, wherein the amino acid sequence is a protein or a salt as follows: the amino acid sequence encoding the protein or the salt contains a mutation resulting from a deletion, substitution or addition of one or more amino acid residues in the sequence, and such the resultant protein and the salt are biologically active and stable, with respect to the protein or its salt having the activity substantially equivalent to that of the coenzyme-binding glucose dehydrogenase.

The protein or its salt, which are the inventive coenzyme-binding glucose dehydrogenase, is preferably one derived from a microorganism having the physicochemical characteristics described above. A microorganism from which the inventive coenzyme-binding glucose dehydrogenase is derived and a microorganism having an ability of producing the inventive coenzyme-binding glucose dehydrogenase may for example be those classified into prokaryotic microorganisms such as genus *Archangium*, genus *Arcaeoglobus*, genus *Arsenophonus*, genus *Ahrensia*, genus *Aureobacterium*, genus *Aerococcus*, genus *Aeropyrum*, genus *Aeromicrobium*, genus *Aeromonas*, genus *Aquifex*, genus *Aquaspirillum*, genus *Aquabacter*, genus *Aquabacterium*, genus *Aquamicrobium*, genus *Actinolloteichus*, genus *Actinokineospora*, genus *Actinocorallia*, genus *Actinosynnema*, genus *Actinosporangium*, genus *Actinobaculum*, genus *Actinobacilus*, genus *Actinopycnidium*, genus *Actinobispora*, genus *Actinoplanes*, genus *Actinopolyspora*, genus *Actinopolymorpha*, genus *Actinomyces*, genus *Actinomadura*, genus *Acrocarpospora*, genus *Agrococcus*, genus *Agrobacterium*, genus *Agromyces*, genus *Agromatium*, genus *Agromonas*, genus *Achromobacter*, genus *Acholeplasma*, genus *Asaia*, genus *Acidianus*, genus *Acidispaera*, genus *Acidiphilium*, genus *Acidimicrobium*, genus *Acidilobus*, genus *Acidaminococcus*, genus *Acidaminobacter*, genus *Acidithiobacillus*, genus *Agitococcus*, genus *Acidothermus*, genus *Acidocella*, genus *Acidobacterium*, genus *Acidovorax*, genus *Acidomonas*, genus *Acinetobacter*, genus *Asiticcacaulis*, genus *Asteroleplasma*, genus *Acetitomaculum*, genus *Acetivibrio*, genus *Acetoanaerobium*, genus *Acetogenium*, genus *Acetothermus*, genus *Acetonema*, genus *Acetobacter*, genus *Acetobacterium*, genus *Acetohalobium*, genus *Acetofilamentum*, genus *Acetomicrobium*, genus *Azoarcus*, genus *Azospira*, genus *Azospirillum*, genus *Azotobacter*, genus *Azonexus*, genus *Azovibrio*, genus *Azomonas*, genus *Azomonotrichon*, genus *Azorhizobium*, genus *Azorhizophilus*, genus *Atopobacter*, genus *Atopobium*, genus *Anaplasma*, genus *Aneurinibacillus*, genus *Anaeroarcus*, genus *Anaerococcus*, genus *Anaerosinus*, genus *Anaerobacter*, genus *Anaerobaculum*, genus *Anaerobispirillum*, genus *Anaerovibrio*, genus *Anaerofilum*, genus *Anaeroplasma*, genus *Anaerobranca*, genus *Anaerovorax*, genus *Anaeromusa*, genus *Anaerorhabdus*, genus *Anoxybacillus*, genus *Abiotrophia*, genus *Afipia*, genus *Amaricoccus*, genus *Amycolata*, genus *Amycolatopsis*, genus *Aminobacter*, genus *Aminobacterium*, genus *Aminomonas*, genus *Amoebobacter*, genus *Ammoniphilus*, genus *Ammonifex*, genus *Amorphosporangium*, genus *Arachnia*, genus *Alysiella*, genus *Alicyclobacillus*, genus *Alishewanella*, genus *Alcanivorax*, genus *Arcanobacterium*, genus *Alcaligenes*, genus *Alkalibacterium*, genus *Alkaliphilus*, genus *Arcobacter*, genus *Arthrobacter*, genus *Alterococcus*, genus *Alteromonas*, genus *Albibacter*, genus *Alloiococcus*, genus *Allochromatium*, genus *Arhodomonas*, genus *Allomonas*, genus *Allorhizobium*, genus *Anacalochloris*, genus *Anacalomicrobium*, genus *Angiococcus*, genus *Angulomicrobium*, genus *Ancylobacter*, genus *Antarctobacter*, genus *Amphibacillus*, genus *Ampullariella*, genus *Ignavigranum*, genus *Idiomarina*, genus *Isochromatium*, genus *Isosphaera*, genus *Ideonella*, genus *Ilyobacter*, genus *Intrasporagium*, genus *Weeksella*, genus *Wigglesworthia*, genus *Williamsia*, genus *Wolinella*, genus *wolbachia*, genus *Ureplasma*, genus *Ureibacillus*, *Eikenella*, genus *Ehrlichia*, genus *Exiguobacterium*, genus *Excellospora*, genus *Ectothiorhodospira*, genus *Aegyptianella*, genus *Eggerthella*, genus *Escherichia*, genus *Edwardsiella*, genus *Ewingella*, genus *Eperythrozonn*, genus *Erysipelothrix*, genus *Erythrobacter*, genus *Erythromicrobium*, genus *Erythromonas*, genus *Elytrosporangium*, genus *Yersinia*, genus *Erwinia*, genus *Eremococcus*, genus *Ensifer*, genus *Enterococcus*, genus *Enterobacter*, genus *Entomoplasma*, genus *Enhydrobacter*, genus *Empedobacter*, *Oenococcus*, genus *Oerskovia*, genus *Oceanimonas*, genus *Oceanospirillum*, genus *Oxalobacater*, genus *Oxalophagus*, genus *Oxobacter*, genus *Octadecabacter*, genus *Ochrobactrum*, genus *Oscillochloris*, genus *Oscillospira*, genus *Obesumbacterium*, genus *Orientia*, genus *Oligella*, genus *Oligotropha*, genus *Oribaculum*, genus *Ornithinicoccus*, genus *Ornithinimicrobium*, genus *Ornithobacterium*, genus *Orenia*, genus *Gardnerella*, genus *Carnimonas*, genus *Carno-* bacterium, genus *Couchioplanes*, genus *Cowdria*, genus *Caulobacter*, genus *Caseobacter*, genus *Catenibacterium*, genus *Catenuloplanes*, genus *Catenococcus*, genus *Catellatospora*, genus *Catonella*, genus *Capsularis*, genus *Capnocytophaga*, genus *Gallionella*, genus *Carvophanon*, genus *Gallicola*, genus *Calymmatobacterium*, genus *Cardiobacterium*, genus *Caldicellulosiruptor*, genus *Caldivirga*, genus *Calderobacterium*, genus *Carboxydibrachium*, genus *Carboxydothermus*, genus *Carbophilus*, genus *Caloramator*, genus *Xanthobacter*, *Xanthomonas*, genus *Xylella*, genus *Xylophilus*, genus *Xenorhabdus*, genus *Kitasatoa*, genus *Kirasatospora*, genus *Chitinophaga*, genus *Kytococcus*, genus *Kineococcus*, genus *Kineosporia*, genus *Quinella*, genus *Kibdelosporangium*, genus *Campylobacter*, genus *Kingella*, genus *Kutzneria*, genus *Cupriavidus*, genus *Craurococcus*, genus *Glaciecola*, genus *Gracilibacillus*, genus *Granulicatella*, genus *Grahamella*, genus *Clavibacter*, genus *Chlamydia*, genus *Chlamydophila*, genus *Cryobacterium*, genus *Glycomyces*, genus *Chrysiogenes*, genus *Cristispira*, genus *Chryseobacterium*, genus *Chryseomonas*, genus *Crinalium*, genus *Cryptosporangium*, genus *Cryprobacterium*, genus *Kluyvera*, genus *Kribbella*, genus *Gluconacetobacter*, genus *Gluconobacter*, genus *Kurthia*, genus *Curtobacterium*, genus *Crenothrix*, genus *Klebsiella*, genus *Clevelandina*, genus *Crossiella*, genus *Clostridium*, genus *Clobicatella*, genus *CHromatium*, genus *Chromobacterium*, genus *Chromohalobacter*, genus *Chloronema*, genus *Chrorobium*, genus *Chloroflexus*, genus *Chloroherpeton*, genus *Caedibacter*, genus *Ketogulonicigenium*, genus *Gemmata*, genus *Gemmiger*, genus *Gemella*, genus *Gemmobacter*, genus *Chelatococcus*, genus *Chelatobacter*, genus *Gelidibacter*, genus *Coenonia*, genus *Coxiella*, genus *Kocuria*, genus *Koserella*, genus *Coprococcus*, genus *Coprothermobacter*, genus *Coprobacillus*, genus *Comamonas*, genus *Coriobacterium*, genus *Corynebacterium*, genus *Collinsella*, genus *Colwellia*, genus *Gordonia*, genus *Conglomeromonas*, genus *Chondromyces*, genus *Thermaerobacter*, genus *Thermus*, genus *Thermacetogenium*, genus *Thermanaerovibrio*, genus *Thermicanus*, genus *Thermithiobacillus*, genus *Thermoactinomyces*, genus *Thermoanaerobacter*, genus *Thermoanaerobacterium*, genus *Thermoanaerobium*, genus *Thermocladium*, genus *Thermocrispum*, genus *Thermocrinis*, genus *Thermochromatium*, genus *Thermococcus*, genus *Thermosipho*, genus *Thermosyntropha*, genus *Thermosphaera*, genus *Thermothrix*, genus *Thermodesulfobacterium*, genus *Thermodesulfovibrio*, genus *Thermodesulforhabdus*, genus *Thermoterrabacterium*, genus *Thermotoga*, genus *Thermonema*, genus *Thermohydrogenium*, genus *Thermobacteroides*, genus *Thermobacillus*, genus *Thermohalobacter*, genus *Thermobispora*, genus *Thermobifida*, genus *Thermofilum*, genus *Thermobranchium*, genus *Thermoplasma*, genus *Thermoproteus*, genus *Thermomicrobium*, genus *Thermomonospora*, genus *Thermoleophilum*, genus *Cytophaga*, genus *Zymobacter*, genus *Zymophilus*, genus *Zymomonas*, genus *Sagittula*, genus *Saccharococcus*, genus *Saccharothrix*, genus *Saccharobacter*, genus *Saccharopolyspora*, genus *Saccharomonospora*, genus *Zavarzinia*, genus *Subtercola*, genus *Saprospira*, genus *Samsonia*, genus *Salinicoccus*, genus *Salinivibrio*, genus *Salibacillus*, genus *Sarcobium*, genus *Sarcina*, genus *Salmonella*, genus *Salegentibacter*, genus *Sanguibacter*, genus *Sandaracinobater*, genus *Dyadobacter*, genus *Dialister*, genus *Dietzia*, genus *Shewanella*, genus *Geothrix*, genus *Geodermatophilus*, genus *Geotoga*, genus *Geobacter*, genus *Geobacillus*, genus *Geovibrio*, genus *Dictyoglomus*, genus *Cycloclasticus*, genus *Psychroserpens*, genus *Psychrobacter*, genus *Cyclobacterium*, genus *Psychroflexus*, genus *Psychromonas*, genus *Sigella*, genus *Dichelobacter*, genus *Dichoromicrobium*, genus *Dysgonomonas*, genus *Cystobacter*, genus *Citrobacter*, genus *Synergistes*, genus *Sinorhizobium*, genus *Diplocalyx*, genus *Simkania*, genus *Simonsiella*, genus *Janibacter*, genus *Janthinobacterium*, genus *Pseudaminobacter*, genus *Pseudoamyclata*, genus *Pseudoalteromonas*, genus *Pseudoxanthomonas*, genus *Pseudocaedibacter*, genus *Pseudonocardia*, genus *Pseudobutyrivibrio*, genus *Pseudomonas*, genus *Pseudoramibacter*, genus *Schwartzia*, genus *Jonesia*, genus *Johnsonella*, genus *Silicibacter*, genus *Syntrophus*, genus *Syntrophococcus*, genus *Syntrophothermus*, genus *Syntrophospora*, genus *Syntrophobacter*, genus *Syntrophobotulus*, genus *Syntrophomonas*, genus *Symbiotes*, genus *Symbiobacterium*, genus *Zoogloea*, genus *Duganella*, genus *Schineria*, genus *Succiniclasticum*, genus *Succinispira*, genus *Succinivibrio*, genus *Succinimonas*, genus *Skermania*, genus *Skermanella*, genus *Starkeya*, genus *Stappia*, genus *Staphylococcus*, genus *Staphylothermus*, genus *Staleya*, genus *Stygiolobus*, genus *Stibiobacter*, genus *Stigmatella*, genus *Stetteria*, genus *Stenotrophomonas*, genus *Stella*, genus *Suttrella*, genus *Suttonella*, genus *Stomatococcus*, genus *Streptoalloteichus*, genus *Streptococcus*, genus *Streptosporangium*, genus *Streptoverticillium*, genus *Streptobacillus*, genus *Streptomyces*, genus *Streptomonospora*, genus *Spirillum*, genus *Spirilliplanes*, genus *Spirillospora*, genus *Spirosoma*, genus *Spiroplasma*, genus *Spirochaeta*, genus *Sphingobacterium*, genus *Sphingobium*, genus *Sphingopyxis*, genus *Sphaerotilus*, genus *Spaerobacter*, genus *Sphingomonas*, genus *Sporichthya*, genus *Sporocytophaga*, genus *Sporosarcina*, genus *Sporotomaculum*, genus *Sporobacter*, genus *Sporobacterium*, genus *Sporohalobacter*, genus *Sporomusa*, genus *Sporolactobacillus*, genus *Smithella*, genus *Slackia*, genus *Sulfitobacter*, genus *Sulfobacillus*, genus *Sulfophobococcus*, genus *Sulfolobus*, genus *Sulfurisphaera*, genus *Sulfurococcus*, genus *Sulforospirillum*, genus *Cedecea*, genus *Setobacterium*, genus *Sebaldella*, genus *Serratia*, genus *Seliberia*, genus *Cellvibrio*, genus *Cerpula*, genus *Serpulina*, genus *Serpens*, genus *Cellulosimicrobium*, genus *Cellulophaga*, genus *Cellulomonas*, genus *Selenihalanaerobacter*, genus *Selenomonas*, genus *Centipeda*, genus *Sodalis*, genus *Zobellia*, genus *Solobacterium*, genus *Thauera*, genus *Dactylosporangium*, genus *Tatumella*, genus *Tatlockia*, genus *Thalassomonas*, genus *Thialkalicoccus*, genus *Thialkalivibrio*, genus *Thialkalimicrobium*, genus *Thiocapsa*, genus *Thiococcus*, genus *Thiodictyon*, genus *Thiocystis*, genus *Thiospira*, genus *Thiospirillum*, genus *Thiosphaera*, genus *Thiothrix*, genus *Thiobacterium*, genus *THiobacillus*, genus *Thiohalocapsa*, genus *Thioflavicoccus*, genus *Thiovulum*, genus *THioploca*, genus *THiopedia*, genus *Thiomargarita*, genus *Thiomicrospira*, genus *Thiomonas*, genus *Thiolamprovum*, genus *Thiorhodococcus*, genus *THiorhodospira*, genus *Thiorhodovibrio*, genus *Tissierella*, genus *Chania*, genus *Tindallia*, genus *Tsukamurella*, genus *Turicella*, genus *Deinococcus*, genus *Deinobacter*, genus *Taylorella*, genus *Tectibacter*, genus *Dechlorosoma*, genus *Dechloromonas*, genus *Tessaracoccus*, genus *Desulfacinum*, genus *Desulfitobacterium*, genus *Desulfocapsa*, genus *Desulfococcus*, genus *Desulfosarcina*, genus *Desulfospira*, genus *Desulfosporosinus*, genus *Desulfocella*, genus *Desulfotalea*, genus *Desulfotignum*, genus *Desulfotomaculum*, genus *Desulfonatronum*, genus *Desulfonatronovibrio*, genus *Desulfonispora*, genus *Desulfonema*, genus *Desulfovirga*, genus *Desufobacter*, genus *Desulfobacterium*, genus *Desulfobacula*, genus *Desulfobacca*, genus *Desulfobulbus*, genus *Desulfohalobium*, genus *Desulfovibrio*, genus *Desulfofustis*, genus *Desulfofaba*, genus *Desulfofrigus*, genus *Desulfomicrobium*, genus *Desulfomonas, genus *Desulfomonile*, genus *Desulforhabdus*, genus *Desulforhopalus*, genus *Desulfurella*, genus *Desulfurococcus*, genus *Desulfurobacterium*, genus *Desulfuromusa*, genus *Desulfuromonas*, genus *Desulfurolobus*, genus *Desemzia*, genus *Dethiosulfovibrio*, genus *Tetragenococcus*, genus *Tetrasphaera*, genus *Denitrobacterium*, genus *Denitrovibrio*, genus *Dehalobacter*, genus *Tepidimonas*, genus *Deferribacter*, genus *Defluvibacter*, genus *Devosia*, genus *Demetria*, genus *Terracoccus*, genus *Terrabacter*, genus *Derxia*, genus *Delftia*, genus *Dermacoccus*, genus *Dermatophilus*, genus *Dermabacter*, genus *Telluria*, genus *Deleya*, genus *Dendrosporobacter*, genus *Toxothrix*, genus *Trabulsiella*, genus *Trichlorobacter*, genus *trichococcus*, genus *Tlumonas*, genus *Treponema*, genus *Dolosigranulum*, genus *Dolosicoccus*, genus *Tropheryma*, genus *Neisseria*, genus *Natrialba*, genus *Natrinema*, genus *Natroniella*, genus *Natronincola*, genus *Natronococcus*, genus *Natronobacterium*, genus *Natronomonas*, genus *NAtronorubrum*, genus *Nannocystis*, genus *Nitrococcus*, genus *Nitrospina*, genus *Nitrospira*, genus *Nitrosococcus*, genus *Nitrosospira*, genus *Nitrosomonas*, genus *Nitorosolobus*, genus *Nitrobacter*, genus *Neochlamydia*, genus *Neorickettsia*, genus *Nesterenkonia*, genus *Nevskia*, genus *Neptunomonas*, genus *Nocardia*, genus *Nocardioides*, genus *Nocardiopsis*, genus *Nonomuraea*, genus *Novosphingobium*, genus *Virgibacillus*, genus *Hydrogenobacter*, genus *Hydrogenovibrio*, genus *Hydrogenophaga*, genus *Hydrogenophilus*, genus *Hyperthermus*, genus *Hyphomicrobium*, genus *Hyphomonas*, genus *Paucimonas*, genus *Bacterionema*, genus *Bacteriovorax*, genus *Bacteroides*, genus *Bactoderma*, genus *Vagococcus*, genus *Pasteuria*, genus *Pasteurella*, genus *Bacillus*, genus *Papillibacter*, genus *Hafnia*, genus *Hahella*, genus *Paracraurococcus*, genus *Parachlamydia*, genus *Paracoccus*, genus *Halanaerobacter*, genus *Halanaerobium*, genus *Paralactobacillus*, genus *Variovorax*, genus *Haliscomenobacter*, genus *Bartonella*, genus *Balneatrix*, genus *Palaeococcus*, genus *Hallella*, genus *Haloarcula*, genus *Haloincola*, genus *Halochromatium*, genus *Halococcus*, genus *Halothermothrix*, genus *Halogeometricum*, genus *Halospirulina*, genus *Halocella*, genus *Halothiobacillus*, genus *Haloterrigena*, genus *Halonatronum*, genus *Halobaculum*, genus *Halobacterium*, genus *Halobacteroides*, genus *Halobacillus*, genus *Halobvibrio*, genus *Haloferax*, genus *Halomethanococcus*, genus *Halomonas*, genus *Halorhabdus*, genus *Halorubrum*, genus *Halorubrobacterium*, genus *Halorhodospira*, genus *Pantoea*, genus *Pandoraea*, genus *Vampirovibrio*, genus *Picrophilus*, genus *Piscirickettsia*, genus *Hippea*, genus *Vitreoscilla*, genus *Bifidobacterium*, genus *Vibrio*, genus *Hymenobacter*, genus *Pimelobacter*, genus *Pilimelia*, genus *Hirschia*, genus *Pirella*, genus *Pirellula*, genus *Pyrococcus*, genus *Pyrodictium*, genus *Pillotina*, genus *Pyrobaculum*, genus *Bilophila*, genus *Pyrolobus*, genus *Faenia*, genus *Facklamia*, genus *Phascolarctobacterium*, genus *Falcivibrio*, genus *Fundibacter*, genus *Finegoldia*, genus *Fibrobacter*, genus *Filibacter*, genus *Filifactor*, genus *Phyllobacterium*, genus *Filobacillus*, genus *Filomicrobium*, genus *Phaeospirillum*, genus *Phenylobacterium*, genus *Ferriacterium*, genus *Ferrimonas*, genus *Fervidobacterium*, genus *Ferroglobus*, genus *Ferroplasma*, genus *Phocoenobacter*, genus *Photobactrium*, genus *Photorhabdus*, genus *Formivibrio*, genus *Fusobacterium*, genus *Buttiauxella*, genus *Butyrivibrio*, genus *Bdellovibrio*, genus *Budvicia*, genus *Phennigia*, genus *Buchnera*, genus *Fusibacter*, genus *Prauserella*, genus *Pragia*, genus *Bracyspira*, genus *Bracymonas*, genus *Bracymonas*, genus *Blastochloris*, genus *Blastococcus*, genus *Blastobacter*, genus *Blastomonas*, genus *Blattabacterium*, genus *Bradyrhizobium*, genus *Frateuria*, genus *Branhamella*, genus *Planococcus*, genus *Planotetraspora*, genus *Planobispora*, genus *Planopolyspora*, genus *Planomicrobium*, genus *Planomonospora*, genus *Flavimonas*, genus *Flavobacterium*, genus *Flammeovirga*, genus *Frankia*, genus *Planctomyces*, genus *Francisella*, genus *Friedmanniella*, genus *Frigoribacterium*, genus *Fluoribacter*, genus *Burkholderia*, genus *Brucella*, genus *Bulleidia*, genus *Flexistipes*, genus *Flexithrix*, genus *Flexibacter*, genus *Flectobacillus*, genus *Plesiomonas*, genus *Brenneria*, genus *Brevundimonas*, genus *Brevinema*, genus *Brevibacterium*, genus *Brevibacillus*, genus *Prevotella*, genus *Prochlorococcus*, genus *Prochlorothrix*, genus *Prochloron*, genus *Brochothrix*, genus *Prosthecochloris*, genus *Prosthecobacter*, genus *Prosthecomicrobium*, genus *Proteus*, genus *Protomonas*, genus *Propionigenium*, genus *Propionispira*, genus *Propionispora*, genus *Propionibacter*, genus *Propionibacterium*, genus *Propionivibrio*, genus *Propioniferax*, genus *Providencia*, genus *Promicromonospora*, genus *Prolinoborus*, genus *Beijejrinckia*, genus *Veillonella*, genus *Beutenbergia*, genus *Beggiatoa*, genus *Pectinatus*, genus *Pectobacterium*, genus *Pediococcus*, genus *Pedobacter*, genus *Pedomicrobium*, genus *Petrotoga*, genus *Paenibacillus*, genus *Beneckea*, genus *Peptococcus*, genus *Peptostreptococcus*, genus *Peptoniphilus*, genus *Haemobartonella*, genus *Haemophilus*, genus *Heliothrix*, genus *HEliobacterium*, genus *Heliobacillus*, genus *HEliophilum*, genus *Heliorestis*, genus *Helicobacter*, genus *Pelistega*, genus *Pelczaria*, genus *Bergeyella*, genus *Helcococcus*, genus *Verrucosispora*, genus *Verrucomicrobium*, genus *Persicobacter*, genus *Herbaspirillum*, genus *Herbidospora*, genus *Herpetosiphon*, genus *Pelodictyon*, genus *Pelospora*, genus *Pelobacter*, genus *Vogesella*, genus *Bogoriella*, genus *Bosea*, genus *Polaribacter*, genus *Polaromonas*, genus *Hollandina*, genus *Polyangium*, genus *Polynucleobacter*, genus *Volcaniella*, genus *Bordetella*, genus *Holdemania*, genus *Porphyrobacter*, genus *Porphyromonas*, genus *Borrelia*, genus *Holospora*, genus *Holophaga*, genus *Hongia*, genus *Meiothermus*, genus *Mycobacterium*, genus *Mycoplasma*, genus *Mycoplana*, genus *Mycetocola*, genus *Myroides*, genus *Magnetospirillum*, genus *Macrococcus*, genus *Macromonas*, genus *Massilia*, genus *Maricaulis*, genus *Marichromatium*, genus *Marinococcus*, genus *Marinitoga*, genus *Marinilabilia*, genus *Marinospirillum*, genus *Marinobacter*, genus *Marinobacterium*, genus *Marinomonas*, genus *Marmoricola*, genus *Malonomonas*, genus *Mannheimia*, genus *Micavibrio*, genus *Myxococcus*, genus *Microellobosporia*, genus *Micrococcus*, genus *Microcyclus*, genus *Microcystis*, genus *Microscilla*, genus *Microsphaera*, genus *Microtetraspora*, genus *Microvirgula*, genus *Microbacterium*, genus *Microbulbifer*, genus *Microbispora*, genus *Micropruina*, genus *Micropolyspora*, genus *Micromonas*, genus *Micromonospora*, genus *Microlunatus*, genus *Mitsuokella*, genus *Megasphaera*, genus *Megamonas*, genus *Mesophilobacter*, genus *Mesoplasma*, genus *Mesorhizobium*, genus *Methanimicrococcus*, genus *Methanocalculus*, genus *Methanoculleus*, genus *Methanogenium*, genus *Methanocorpusculum*, genus *Methanococcoides*, genus *Methanococcus*, genus *Methanothermus*, genus *Methanothermobacter*, genus *Methanosaeta*, genus *Methanosarcina*, genus *Methanospirillum*, genus *Methanosphaera*, genus *Methanothrix*, genus *Methanobacterium*, genus *Methanohalobium*, genus *Methanohalophilus*, genus *Methanopyrus*, genus *Methanofollis*, genus *Methanoplanus*, genus *Methanoburevibacter*, genus *Methanomicrobium*, genus *Methanolacinia*, genus *Methanolobus*, genus *Methallosphaera*, genus *Methylarcula*, genus *Methylocaldum*, genus *Methylococcus*, genus *Methylcarcina*, genus *Methylocystis*, genus

*Methylosinus*, genus *Methysphaera*, genus *Methylcella*, genus *Methylbacter*, genus *Methylbacterium*, genus *Methylobacillus*, genus *Methylopila*, genus *Methylophaga*, genus *Methylpholus*, genus *Methylovorus*, genus *Methylmicrobium*, genus *Methylomonas*, genus *Methylorhabdus*, genus *Meniscus*, genus *Melittangium*, genus *Melissococcus*, genus *Moellerella*, genus *Moorella*, genus *Mogibacterium*, genus *Modestobacter*, genus *Mobiluncus*, genus *Moraxella*, genus *Morganella*, genus *Mortiella*, genus *Morococcus*, genus *Eubacterium*, genus *Iodobacter*, genus *Yokenella*, genus *Rahnella*, genus *Raoultella*, genus *Lactococcus*, genus *Lactosphaera*, genus *Lactobacillus*, genus *Lachnospira*, genus *Rathayibacter*, genus *Rhabdochromatium*, genus *Labrys*, genus *Ralstonia*, genus *Rarobacter*, genus *Lamprocystis*, genus *Lamprobacter*, genus *Lampropedia*, genus *Riemerella*, genus *Rickettsia*, genus *Rickettsiella*, genus *Rikenella*, genus *Listeria*, genus *Listonella*, genus *Lysobacter*, genus *Rhizobacter*, genus *Rhizobium*, genus *Rhizomonas*, genus *Lyticum*, genus *Limnobacter*, genus *Lewinella*, genus *Ruegeria*, genus *Rugamonas*, genus *Lucibacterium*, genus *Luteimonas*, genus *Luteococcus*, genus *Runella*, genus *Rubrivivax*, genus *Rubrimonas*, genus *Rubrobacter*, genus *Ruminococcus*, genus *Ruminobacter*, genus *Leifsonia*, genus *Leclercia*, genus *Lechevalieria*, genus *Legionella*, genus *Renibacterium*, genus *Levinea*, genus *Leptospira*, genus *Leptospirillum*, genus *Leptothrix*, genus *Leptotrichia*, genus *Leptonema*, genus *Leminorella*, genus *Lentzea*, genus *Leucothrix*, genus *Leuconostoc*, genus *Leucobacter*, genus *Lawsonia*, genus *Lautropia*, genus *Lochalimaea*, genus *Roseateles*, genus *Roseinatronobacter*, genus *Roseibium*, genus *Roseivivax*, genus *Roseococcus*, genus *Roseospira*, genus *Roseospirillum*, genus *Roseobacter*, genus *Roseovarius*, genus *Roseomonase*, genus *Roseburia*, genus *Rhodanobacter*, genus *Rothia*, genus *Rhodococcus*, genus *Rhodothermus*, genus *Rhodocyclus*, genus *Rhodocista*, genus *Rhodopseudomonas*, genus *Rhodospira*, genus *Rhodospirillum*, genus *Rhodothalassium*, genus *Rhodobaca*, genus *Rhodobacter*, genus *Rhodobium*, genus *Rhodovibrio*, genus *Rhodopila*, genus *Rhodoferax*, genus *Rhodoplanes*, genus *Rhodovulum*, genus *Rhodomicrobium*, genus *Lonepinella*, genus *Weissella*, genus *Waddlia* and the like.

Those which can also be exemplified are eukaryotic microorganisms such as genus *Issatchenkia*, *Candida*, genus *Cryptococcus*, genus *Kluyverintces*, genus *Kloeckera*, genus *Saccharomycodes*, genus *Saccharomyces*, genus *Zygosaccharomyces*, genus *Shizosaccharomyces*, genus *Sirobasidium*, genus *Strigmatomyces*, genus *Sporidobolus*, genus *Sporobolomyces*, genus *Dekkera*, genus *Debaryomyces*, genus *Trichosporon*, genus *Trigonopsis*, genus *Torulaspora*, genus *Tremella*, genus *Nadsonia*, genus *Nematospora*, genus *Hanseniaspora*, genus *Pichia*, genus *Fibulobasidium*, genus *Filobasidium*, genus *Filobasidiella*, genus *Bullera*, genus *Brettanomyces*, genus *Holtermannia*, genus *Malassezia*, genus *Metschnikowia*, genus *Lipomyces*, genus *Leucosporidium*, genus *Rhodosporidium*, genus *Rhodotorula*, genus *Acaulopage*, genus *Aquamortierella*, genus *Asellaria*, genus *Amoebidium*, genus *Amoeophilus*, genus *Arundinula*, genus *Utharomyces*, genus *Echinosporangium*, genus *Enterobryus*, genus *Endogone*, genus *Entomophthora*, genus *Kickxella*, genus *Genistellospora*, genus *Choanephora*, genus *Coemansia*, genus *Cochlonema*, genus *Conidiobolus*, genus *Saksenaea*, genus *Thamnidium*, genus *Thamnocephalis*, genus *Dispira*, genus *Dimargaris*, genus *Syncephalastrum*, genus *Syncephalis*, genus *Zoopage*, genus *Sclerocystis*, genus *Smittium*, genus *Basidiobolus*, genus *Parataeniella*, genus *Paramoebidium*, genus *Palavascia*, genus *Harpella*, genus *Piptocephalis*, genus *Pilobolus*, genus *Phycomyces*, genus *Blakeslea*, genus *Hesseltinella*, genus *Helicocephalum*, genus *Mycotypha*, genus *Radiomyces*, genus *Legeriomyces*, genus *Rhopalomyces*, genus *Acrasis*, genus *Acytostelium*, genus *Arcyria*, genus *Echinostelium*, genus *Echinosteliopsis*, genus *Oligonema*, genus *Cavostelium*, genus *Guttulinopsis*, genus *Clastoderma*, genus *Cribraria*, genus *Coenonia*, genus *Copromyxa*, genus *Comatricha*, genus *Colloderma*, genus *Dianema*, genus *Dictyostelium*, genus *Didymium*, genus *Diderma*, genus *Stemonitis*, genus *Thraustochytrium*, genus *Ceratiomyxa*, genus *Ceratiomyxella*, genus *Trichia*, genus *Physarum*, genus *Plasmodiophrora*, genus *Fuligo*, genus *Bursulla*, genus *Prorostelium*, genus *Protosporangium*, genus *Hemitrichia*, genus *Perichaena*, genus *Polysphondylium*, genus *Polymyxa*, genus *Labyrinthula*, genus *Lamproderma*, genus *Lycogala*, genus *Licea*, genus *Wardmyces*, genus *Actinopelte*, genus *Asterosporium*, genus *Arthrinium*, genus *Alternaria*, genus *Oidium*, genus *Clabosporium*, genus *Cladobotryum*, genus *Graphium*, genus *Colletotrichum*, genus *Sclerotium*, genus *Stagonospora*, genus *Stibella*, genus *Tubercularia*, genus *Bactridium*, genus *Pycnothrium*, genus *Phaeoisaria*, genus *Pestalozziella*, genus *Rhizoctonia*, genus *Rhinocladiella*, genus *Leptothyrium*, genus *Achlyogeton*, genus *Anisolpidium*, genus *Albugo*, genus *Ectrogella*, genus *Olipidium*, genus *Olpidiopsis*, genus *Catenaria*, genus *Chytridium*, genus *Cladochytrium*, genus *Coelomomyces*, genus *Gonapodya*, genus *Saprolegnia*, genus *Sirolpidium*, genus *Synchytrium*, genus *Haliphthoros*, genus *Harpochytrium*, genus *Pythium*, genus *Hyphochytrium*, genus *Physoderma*, genus *Phlyctidium*, genus *Blastocladia*, genus *Peronospora*, genus *Peronophythora*, genus *Micormycopsis*, genus *Megachytrium*, genus *Monoblepharis*, genus *Lagenidium*, genus *Rhizidiomyces*, genus *Rhizidium*, genus *Rhipidium*, genus *Leptomitus*, genus *Leptolegniella*, genus *Acremonium*, genus *Aspergillus*, genus *Absidia*, genus *Arachniotus*, genus *Arthrobotrys*, genus *Ulocladium*, genus *Echinobotryum*, genus *Exophiala*, genus *Epicoccum*, genus *Oidiodendron*, genus *Oedocephalum*, genus *Aureobasidium*, genus *Curvularia*, genus *Candelabrella*, genus *Cunninghamella*, genus *Gymnoascus*, genus *Cladosporium*, genus *Graphium*, genus *Gliocladium*, genus *Chrysosporium*, genus *Chromelosporium*, genus *Geotrichum*, genus *Geomyces*, genus *Chaetomium*, genus *Geniculifera*, genus *Gonatobotrysm*, genus *Coniothyrium*, genus *Circinella*, genus *Zygorhynchus*, genus *Diplodia*, genus *Cylindrocarpon*, genus *Scopulariopsis*, genus *Stachybotrys*, genus *Stemphylium*, genus *Sporothrix*, genus *Sepedonium*, genus *Dactylella*, genus *Talaromyces*, genus *Dratomyces*, genus *Trichurus*, genus *Trichocladium*, genus *Trichothecium*, genus *Trichoderma*, genus *Trichophyton*, genus *Nigrospora*, genus *Verticicladiella*, genus *Verticillium*, genus *Paecilomyces*, genus *Pithomyces*, genus *Bipolaris*, genus *Pyrenochaeta*, genus *Phialocephala*, genus *Phialophora*, genus *Phoma*, genus *Fusarium*, genus *Pestalotiopsis*, genus *Penicillium*, genus *Botrytis*, genus *Microsporum*, genus *Myrothecium*, genus *Mucor*, genus *Memnoniella*, genus *Monacrosporium*, genus *Monilia*, genus *Mortierella*, genus *Eupenicillium*, genus *Eurotium*, genus *Rhizopus*, genus *Leptographium*, genus *Robillarda*, genus *Austroboletus*, genus *Auricularia*, genus *Auriscalpium*, genus *Agaricus*, genus *Agrocybe*, genus *Asterophona*, genus *Astraeus*, genus *Aseroe*, genus *Anellaria*, genus *Amauroderma*, genus *Amanita*, genus *Armillaria*, genus *Armillariella*, genus *Alcuria*, genus *Ischnoderma*, genus *Inocybe*, genus *Inonotus*, genus *Ileodictyon*, genus *Wynnea*, genus *Verpa*, genus *Volvariella*, genus *Urnula*, genus *Echinodontium*, genus *Exidia*, genus Elfvingia, genus Oudemansiella, genus Omphalina, genus Onnia, genus Catathelasma, genus Ganoderma, genus Camarophyllus, genus Chalciporus, genus Galerina, genus Calocera, genus Calostoma, genus Cantharellus, genus Cantharellula, genus Cyathus, genus Cyclomyces, genus Cystoderma, genus Cyptotrama, genus Cymatoderma, genus Gymnopilus, genus Kuehneromyces, genus Gyrodon, genus Gyroporus, genus Gyromitra, genus Guepinia, genus Xanthoconium, genus Xylaria, genus Xerocomus, genus Xeromphalina, genus Cudonia, genus Clavatia, genus Clavaria, genus Clavariadelphus, genus Clavicorona, genus Clavulina, genus Clavulinopsis, genus Craterellus, genus Clathrus, genus Clitocybe, genus Clitopilus, genus Crinipellis, genus Grifola, genus Cryptoderma, genus Cryptoporus, genus Crucibulum, genus Creolophus, genus Crepidotus, genus Chroogomphus, genus Chlorosplenium, genus Geastrum, genus Geolossum, genus Cotylidia, genus Conocybe, genus Kobayashia, genus Coprinus, genus Gomphidius, genus Gomphus, genus Coriolus, genus Cordyceps, genus Cortinarius, genus Coltricia, genus Collybia, genus Sarcoscypha, genus Sarcodon, genus Sarcodontia, genus Suillus, genus Schizophyllum, genus Squamanita, genus Scutellinia, genus Scleroderma, genus Stereum, genus Strobilomyces, genus Stropharia, genus Spathularia, genus Sparassis, genus Daedaleopsis, genus Dacryomyces, genus Daldinia, genus Dictyophora, genus Tylopilus, genus Tyromyces, genus Descolea, genus Thelephora, genus Tulostoma, genus Trametes, genus Trichoglossum, genus Torichocoma, genus Tricoloma, genus Tricholomopsis, genus Tremella, genus Tremellodon, genus Naematoloma, genus Nidula, genus Neobulgaria, genus Baeospora, genus Paxillus, genus Battarea, genus Panaeolus, genus Panus, genus Panellus, genus Bankera, genus Hygrocybe, genus Hygrophorus, genus Hygrophoropsis, genus Bisporella, genus Pisolithus, genus Hydnum, genus Hydnellum, genus Hypsizygus, genus Piptoporus, genus Hypoxylon, genus Hymenochaete, genus Hirschioporus, genus Pyrrhoderma, genus Favolus, genus Phaeolus, genus Phaeolepiota, genus Phallus, genus Fistulina, genus Phyllotopsis, genus Phylloporus, genus Filoboletus, genus Phellinus, genus Fomitopsis, genus Fomes, genus Pholiota, genus Psathyrella, genus Psilocybe, genus Pseudocolus, genus Pseudohiatula, genus Prerula, genus Flammulina, genus Pulveroboletus, genus Bulgaria, genus Pluteus, genus Pleurocybella, genus Pleurotus, genus Plectania, genus Phlogiotis, genus Peziza, genus Penicilliopsis, genus Hebeloma, genus Hericium, genus Helvella, genus Podostroma, genus Polyozellus, genus Polyporus, genus Polyporellus, genus Holtermannia, genus Boibitius, genus Porphyrellus, genus Boletinus, genus Boletellus, genus Boletus, genus Boletopsis, genus Porodisculus, genus Bondarzewia, genus Macrocystidia, genus Macropodia, genus Macrolepiota, genus Marasmius, genus Marasmiellus, genus Microporus, genus Mycena, genus Mitrula, genus Mutinus, genus Melanoleuca, genus Merulius, genus Morchella, genus Laetiporus, genus Lactarius, genus Lasiosphaera, genus Laccaria, genus Ramaria, genus Lampteromyces, genus Lyophyllum, genus Rigidoporus, genus Lycoperdon, genus Rhizina, genus Lysurus, genus Limacella, genus Linder, genus Russula, genus Leucocoprinus, genus Leucopaxillus, genus Leotia, genus Resupinatus, genus Leccinum, genus Lepiota, genus Lepista, genus Lenzites, genus Lentaria, genus Lentinus, genus Lentinula, genus Lentinellus, genus Rozites, genus Rhodocybe, genus Rhodotus, genus Rhodophyllus and the like.

A microorganism listed above which has an ability of producing an inventive coenzyme-binding glucose dehydrogenase has been deposited under its accession number to IFO, ATCC and the like, and can be obtained from known distributors and corporations. Such a microorganism may for example be a eukaryotic microorganism, more preferably mycotic microorganism. It is also possible to use the microorganism which is designated as "97508" and was deposited under FERM BP-08578 to International Patent Organism Depositary of National Institute of Advanced Industrial Science and Technology.

In one embodiment of the method for producing the inventive coenzyme-binding glucose dehydrogenase, a microorganism having an ability of producing the inventive coenzyme-binding glucose dehydrogenase is cultured in a nutrition medium, in which the coenzyme-binding glucose dehydrogenase is allowed to be produced and accumulated, and then recovered to yield a protein which is the coenzyme-binding glucose dehydrogenase and its salt.

The deposited inventive strain FERM BP-08578, a coenzyme-binding glucose dehydrogenase derived therefrom, and a method for obtaining the enzyme are described below.
1. Physicochemical Characteristics of FERM BP-08578-Derived Enzyme
(1) Effect: On the basis of the classification by International Union of Biochemistry (IUB), the inventive enzyme corresponds to EC1.1.99.10, and catalyzes the reaction shown below which oxidizes a hydroxyl group in the 1st-position of glucose in the presence of an electron acceptor to yield glucono-δ-lactone.

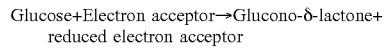

Glucose+Electron acceptor→Glucono-δ-lactone+ reduced electron acceptor

In the invention, the electron acceptor may for example be phenazine methosulfate, 1-methoxy-5-methylphenazinium methyl sulfate, 2,6-dichlorophenolindophenol, ferricyanides and the like.
(2) Substrate specificity: The relative reactivity (substrate specificity) of the inventive enzyme when using D-glucose and other substrates (all at the final concentration of 333 mM except for D-cellobiose at 193 mM, D-trehalose and D-raffinose at 121 mM) by the activity measurement method 1 described below are shown in Table 1. The relative reactivity (substrate specificity) when using D-glucose and maltose at the final concentrations of 550 mM and 100 mM are shown in Table 2. A higher activity was observed on D-glucose, while lower activity were observed on D-mannose, 1,5-anhydro-D-glucitol, D-cellobiose, D-trehalose, maltose, D-galactose, D-glucose-6-phosphate and D-fructose. Almost no activity was observed on L-arabinose, lactose, D-sorbitol, gluconic acid, sucrose, D-mannitol, L-sorbose, D-ribose, L-rhamnose, D-glucose-1-phosphate, D-raffinose, ethanol or glycerol.
(3) Optimum pH: pH7.0 to pH9.0.
(4) pH for stability: pH4.5 to pH8.5.
(5) Optimum temperature: Approximately 55° C.
(6) Thermal stability: Stable at 50° C. or below.
(7) Molecular weight: About 130 kDa when measured by a gel filtration method, and about 85 kDa when measured by a sodium dodecyl sulfate-polyacrylamide gel electrophoresis.
(8) Km value: 49.7 mM (D-glucose).
(9) Isoelectric point: The isoelectric point (pI) of the coenzyme-binding glucose dehydrogenase measured by an isoelectric focusing was about 4.4.
(10) Inhibitor: When each additive was added at 1 mM as a final concentration to the activity measurement method 1 described below and the activity was measured, an inhibitory effect of each additive was observed when comparing with the control group as shown in Table 3. When adding 1,10-phenanthroline (dissolved in methanol) at each final concentration to the activity measurement method 1 described below, the inhibitory effect shown in Table 4 was observed. The activity of this enzyme was inhibited potently by heavy metal ions (Ag+, $Cu^{2+}$, $Hg^{2+}$), and inhibited by 60% or higher by 1,10-phenanthroline, proflavin and $Mn^{2+}$.

(11) Coenzyme: Flavin adenine dinucleotide.

The amino acid sequence of the coenzyme-binding glucose dehydrogenase and the base sequence of a gene encoding it are also encompassed by the invention.

For producing the inventive coenzyme-binding glucose dehydrogenase, a microorganism for producing the coenzyme-binding glucose dehydrogenase may be any microorganism as far as it can produce the inventive coenzyme-binding glucose dehydrogenase, and the enzyme can efficiently be produced by using a microorganism, preferably a eukaryotic microorganism, more preferably a mycotic microorganism. It is especially preferred to use the microorganism which is designated as "97508" and was deposited under FERM BP-08578 to International Patent Organism Depositary of National Institute of Advanced Industrial Science and Technology. The deposited strain was isolated from a soil by Applicants, and has the mycological characteristics as described below. In the invention, any variant of the strain mentioned above may also be employed. Such a variant can be obtained for example by the irradiation with an ultraviolet light or X-ray or the treatment with a chemical modifier (NTG and the like).

2. Mycological Characteristics of FERM BP-08578

(1) Morphological characteristics: The morphological profile of the present strain when observed by an optical microscope after allowed to grow on a potato dextrose agar medium is described below. Each mycelium has a width of 2 μm to 4 μm, and has a regular septum. Most of the mycelia grow linearly, and have branches with almost no swollen mycelia being observed. Several mycelia are gathered together to form a mycelial bundle. The mycelial width is almost constant. The surface of a mycelium is smooth and the septum is slightly thick. A crystalloid is formed around the root of the aerial mycelia. No clamp connection is formed. The mycotic body formed in 2-week culture exhibited no formation of any sexual or asexual reproductive organs, and no oidia or thick-walled spores are present.

(2) Growth condition in various culture media: On all agar plates, each mycelium is in a form of a fluff. The aerial mycelium shade is white. On the potato dextrose agar plate, the backside color is pale orange to orange. The growth magnitude is medium, and a colony after culturing at 25° C. for 1 week has a diameter of 30 mm to 35 mm on the potato dextrose and oatmeal agar plates, and 37 mm to 38 mm on the malt extract agar plate. The production of soluble pigments of a pale yellow color on the potato dextrose agar plate and a slightly reddish to grey-reddish color on the oatmeal agar plate was noted. The mycotic body formed in 2-week culture exhibited no formation of reproductive organs such as a conidiophore, and no exudate was produced.

(3) Physiological characteristics: The present strain is an aerobic one and has an optimum growth temperature of about 37° C. on the potato dextrose agar plate.

3. Taxonomical Characteristics of FERM BP-08578

Based on the characteristics described above, the deposited strain "97508" was characterized with referring to Ainsworth & Bisby's Dictionary of the Fungi, 7th edition (Ed. by Hawksworth, Sutton, Ainsworth). As a result of this characterization, the deposited strain was revealed to be a microorganism classified into the genus *Aspergillus*. Then its genome sequence was subjected to BLAST homology search. An 18S rDNA fragment was amplified using a genome DNA as a template by PCR method, and then sequence of the purified PCR product was analyzed. In order to search for an analogous base sequence through GenBank (GenBank/EMBL/DDBJ international DNA sequence database), BLAST (Altschul et al., 1997) homology search was conducted, and revealed that this deposited strain "97508" is *Aspergillus terreus*.

In one embodiment of the method for producing a coenzyme-binding glucose dehydrogenase according to the invention, the microorganism described above is cultured to allow the coenzyme-binding glucose dehydrogenase to be expressed or produced by the microorganism in internal and/or external of its fungus body.

For the culture of the microorganism in the invention, any ordinary culture medium for microorganism may be used. Such medium may include a synthetic or natural medium, as long as it contains suitable amounts of carbon sources, nitrogen sources, inorganic substances and other trace elements required by the microorganism. The carbon sources may be glucose, sucrose, dextrin, starch, glycerin, syrup and the like. The nitrogen sources may be inorganic salts such as ammonium chloride, ammonium nitrate, ammonium sulfate and ammonium phosphate, amino acids such as DL-alanine and L-glutamic acid, as well as nitrogen-containing natural materials such as peptone, meat extract, yeast extract, malt extract, corn steep liquor and the like. The inorganic materials may for example be monosodium phosphate, disodium phosphate, monopotassium phosphate, dipotassium phosphate, magnesium sulfate, ferric chloride and the like.

The culture in order to obtain the inventive coenzyme-binding glucose dehydrogenase is conducted preferably in an aerobic condition for example by a shaking or aerating culture at a temperature of 25° C. to 60° C. at a pH of 5 to 8. The culture period ranges preferably from 2 days to 4 days. As a result of such a culture, the coenzyme-binding glucose dehydrogenase can be produced and accumulated in the culture, especially in a culture fluid. By using this culture method, the coenzyme-binding glucose dehydrogenase can be produced by the microorganism and accumulated also internal fungus body. Subsequently, the coenzyme-binding glucose dehydrogenase can be recovered from the culture by means of an ordinary protein purification method. Such a method may be a method comprising incubating the microorganism followed by removing the microorganism for example by a centrifugation to obtain a supernatant, or a method comprising incubating the microorganism, recovering the cultured microorganism from the culture fluid by a centrifugation, crushing the cultured microorganism by a suitable method, and then isolating a supernatant for example by a centrifugation from the pelletized microorganism fluid. The coenzyme-binding glucose dehydrogenase contained in such a supernatant can be purified by a combination of suitable purification procedures such as salting out, solvent sedimentation, dialysis, ion exchange chromatography, hydrophobic adsorption chromatography, gel filtration, affinity chromatography, electrophoresis and the like.

In the culture for obtaining the inventive coenzyme-binding glucose dehydrogenase, a solid medium can be also used. The method for such a culture is not limited particularly, and may for example be a static culture, or a dynamic culture involving a continuous agitation of the culture, such as a rotational culture or fluidized bed culture, with a static culture being preferred due to a less expensive investment in equipment. Thereafter, as a method of obtaining the coenzyme-binding glucose dehydrogenase from the culture, an ordinary protein purification method can be adopted. That is, the culture is combined with water or other extraction medium and shaken, made free of any solid components such as bran by means of a centrifugation or filtration, thereby yielding an extract. It is also possible that the coenzyme-binding glucose dehydrogenase accumulated in the fungus bodies can be recovered by grinding the culture residue after obtaining the extract described above together with a an abrasive compound such as a sea sand, followed by adding water to extract the coenzyme-binding glucose dehydrogenase released from the fungus bodies. In order to obtain the entire coenzyme-binding glucose dehydrogenase, the entire culture is ground with an abrasive compound such as a sea sand, followed by adding water to extract both of the coenzyme-binding glucose dehydrogenase released from the fungus bodies and the coenzyme-binding glucose dehydrogenase secreted into the culture all at once. The coenzyme-binding glucose dehydrogenase contained in such a supernatant can be purified by a combination of suitable purification procedures such as salting out, solvent sedimentation, dialysis, ion-exchange chromatography, hydrophobic adsorption chromatography, gel filtration, affinity chromatography, electrophoresis and the like.

Alternatively, the inventive coenzyme-binding glucose dehydrogenase may also be a synthetic coenzyme-binding glucose dehydrogenase or a recombinant coenzyme-binding glucose dehydrogenase obtained by a gene engineering technology. Those skilled in the art can obtain the coenzyme-binding glucose dehydrogenase readily based on the disclosure of the protein or its salt derived from the physicochemical characteristics of the inventive coenzyme-binding glucose dehydrogenase. For example, the coenzyme-binding glucose dehydrogenase can be extracted from a microorganism including a fungi or a naturally occurring material such as an animal or plant, or can be obtained synthetically with referring to the amino acid sequence or the base sequence of the gene encoding it. Moreover, it is also possible to produce the coenzyme-binding glucose dehydrogenase industrially using a gene engineering method in which a gene segment of the coenzyme-binding glucose dehydrogenase gene is inserted into a known expression vector such as a commercial expression vector and then the resultant plasmid is used to transform a host such as *Escherichia coli* to obtain a transformant which is then cultured to obtain a target coenzyme-binding glucose dehydrogenase.

For measuring the activity of the inventive enzyme, the enzyme is diluted appropriately to a final concentration of 0.1 to 1 unit/ml. The enzymatic activity unit of the enzyme is the enzymatic activity enabling the oxidation of 1 µmol glucose per minute. The enzymatic activity of the inventive coenzyme-binding glucose dehydrogenase can be measured by the method shown below.

(i) Enzymatic Activity Measurement Method 1

To a 3-ml quartz cell (light path length: 1 cm), 1.0 ml of 0.1M potassium phosphate buffer (pH7.0), 1.0 ml of 1.0M D-glucose, 0.1 ml of 3 mM 2,6-dichlorophenolindophenol (hereinafter referred to as DCIP), 0.2 ml of 3 mM 1-methoxy-5-methylphenazinium methyl sulfate and 0.65 ml of water are added, which is followed by setting in a thermostat cell holder-mounted spectrophotometer and incubated at 37° C. for 5 minutes and then supplemented with 0.05 ml of the enzyme solution, and then measuring the change in the absorption of DCIP at 600 nm ($\Delta$ABS/min). Based on a molar extinction coefficient of DCIP at pH7.0 being regarded as $16.3 \times 10^3$ cm$^{-1}$M$^{-1}$ and the enzymatic activity corresponding to the reduction of 1 µmol of DCIP per minute being equivalent to 1 unit of the enzymatic activity, the enzymatic activity was determined from the change in the absorption on the basis of the following equation.

$$\text{Enzymatic activity (unit/ml)} = (-\Delta ABS/16.3) \times (3.0/0.05) \times \text{Enzyme dilution rate}$$

(ii) Enzymatic Activity Measurement Method 2

It was carried out that 3.4 µl of 1.0 M potassium phosphate buffer (pH7.0), 0.1 ml of 1.0 M D-glucose and 86.6 µl of 20 mM DCIP were incubated at 37° C. for 5 minutes, supplemented with 0.01 ml of an enzyme solution, stirred, reacted for 5 minutes, incubated at 100° C. for 3 minutes to quench the reaction. Thereafter, 0.19 ml of 100 mM glycine-sodium buffer (pH13.0), 0.01 ml of 2.0N potassium hydroxide were added, incubated at 37° C. for 10 minutes to convert D-gluconic acid in the solution into D-glucono-δ-lactone, and thereafter combined with 0.39 ml of a 100 mM Tris-HCl buffer (pH7.5) and 0.01 ml of 1.0N hydrochloric acid to achieve a neutral pH. The D-gluconic acid in the solution was quantified using the D-gluconic acid/D-glucono-δ-lactone measurement kit (Boehringer Mannheim). Since the enzymatic activity corresponding to the production of 1 µmol of D-glucono-δ-lactone per minute is equivalent substantially to 1 unit of this enzyme, this enzymatic activity was determined based on the amount of D-glucono-δ-lactone produced.

The invention relates to a material production and an analytical application employing an inventive coenzyme-binding glucose dehydrogenase, and also relates to the use in the modification of pharmaceutical or food product materials. In one example, the use is made in a method for eliminating glucose in a sample containing a biological material using the coenzyme-binding glucose dehydrogenase as a reagent, a measurement method as well as in such a reagent or a reagent composition. The use is made also in a method for producing an organic compound using the inventive coenzyme-binding glucose dehydrogenase as well as in a basic ingredient therefor.

The inventive coenzyme-binding glucose dehydrogenase is the enzyme that catalyzes a reaction for oxidizing glucose in the presence of an electron acceptor. In the invention, the reaction mentioned above employs the inventive coenzyme-binding glucose dehydrogenase. Such a coenzyme-binding glucose dehydrogenase is not limited particularly, and is preferably a coenzyme-binding glucose dehydrogenase derived from a eukaryotic microorganism producing the coenzyme-binding glucose dehydrogenase, with a coenzyme-binding glucose dehydrogenase derived from a mycotic microorganism being preferred especially.

Now the description is made with regard to the application of the coenzyme-binding glucose dehydrogenase obtained according to the invention. Since the coenzyme-binding glucose dehydrogenase is the enzyme that catalyzes a reaction for oxidizing glucose in the presence of an electron acceptor, any application in which the change resulting from such a reaction can be utilized can be mentioned. For example, the coenzyme-binding glucose dehydrogenase can be used in a reagent for measuring or eliminating glucose in a sample containing a biological material. It is also possible to use in medical and clinical fields, and also in the material production and analysis employing the coenzyme-binding glucose dehydrogenase.

The inventive biosensor may be any sensor having a reaction layer containing the inventive coenzyme-binding glucose dehydrogenase as an enzyme. For example, the biosensor can be produced in a method wherein an enzymatic reaction layer formed thereon containing a hydrophilic polymer, a redox enzyme and an electron acceptor is brought into contact with an electrode system consisting of an action electrode, a counter electrode and a reference electrode is formed for example by a screen printing on an insulating board. When a substrate-containing sample solution is dropped onto the enzymatic reaction layer in this biosensor, the enzymatic reaction layer is dissolved to effect the reaction between the enzyme and the substrate, thereby reducing the electron acceptor. After completion of the enzymatic reaction, the reduced electron acceptor is oxidized electrochemically, whereupon the biosensor can measure the concentration of the substrate in the sample based on the resultant oxidation current value. Otherwise, a biosensor can be constructed so that the chromogenic intensity or pH change is detected. By using above mentioned biosensors, any of various materials can be measured by selecting the enzyme whose substrate is the target substance. For example, when the inventive coenzyme-binding glucose dehydrogenase is selected as an enzyme, a glucose sensor enabling the measurement of the concentration of glucose in a sample solution can be produced.

As the electron acceptor in the biosensor, a chemical substance having an excellent ability of transferring an electron can be employed. Such a chemical substance having an excellent ability of transferring an electron is generally a substance referred to as "electron carrier", "mediator" or "oxidation/reduction(redox)-mediating agent", such as the electron transfer and the redox-mediating agent listed in JP-W-2002-526759.

In the biosensor, an inexpensive potassium ferricyanide (potassium hexacyanoferrate (III)) is generally employed as an electron acceptor, and usually used at a final concentration of 1 mM or less. Nevertheless, the inventive coenzyme-binding glucose dehydrogenase enables a more sensitive measurement of D-glucose when using potassium ferricyanide at a concentration as high as 2 to 500 mM, more preferably 30 to 100 mM. A preferred embodiment of the inventive measurement method, measurement reagent, measurement compound, biosensor and the like is characterized by the use of potassium ferricyanide in its relevant measurement system at a final concentration of 2 to 500 mM.

EXAMPLES

The present invention is further described in the following Examples, by which the invention is not restricted without departing from its scope. In the following Examples, the quantification of a coenzyme-binding glucose dehydrogenase was conducted as described above.

Example 1

Culture of Deposited Strain 97508

100 ml of a culture medium (pH6.0) containing 1% glucose (WAKO PURE CHEMICAL), 2% defatted soybean (NIPPON SHOKUHAN), 0.5% of corn steep liquor (KYODO SHOJI) and 0.1% magnesium sulfate (Nacalai Tesque) was placed in a 500-ml culture flask, which was sterilized at 121° C. for 20 minutes, cooled, inoculated with a platinum loop of the deposited strain 97508, shaken at 30° C. for 88 hours to obtain a seed culture of the strain. 4 L of the culture medium having the composition similar to that described above but supplemented with an antifoam agent was added to a 5-L jar fermenter, which was sterilized at 121° C. for 30 minutes, cooled, inoculated with 40 ml of the seed culture described above, cultured at 28° C. for 31 hours with aerating and shaking to obtain a preliminary culture of the strain. Then, 160 L of the culture medium having the composition similar to that described above but supplemented with an antifoam agent was added to a 200-L jar fermenter, which was sterilized at 121° C. for 20 minutes, cooled, inoculated with 1.6 L of the preliminary culture described above, cultured at 28° C. for 41 hours with aerating and shaking. After completion of the culture, the culture fluid was centrifuged to obtain the supernatant.

Example 2

Isolation of Coenzyme-Binding Glucose Dehydrogenase from the Culture Supernatant By the following Steps 2.1 to 2.5, the coenzyme-binding glucose dehydrogenase was isolated.

2.1 Concentration

160 L of the culture supernatant of Example 1 was concentrated through an ultrafiltration membrane "Pellicon 2 Module" (Millipore), and transferred into a 20 mM potassium phosphate buffer (pH7.5) to obtain a crude enzyme solution.

2.2 Purification by Butyl-TOYOPEARL 650M (TOSOH) (First Process)

The abovementioned crude enzyme solution was prepared in 65%-saturated ammonium sulfate (pH7.5), and centrifuged to obtain a supernatant. This treated crude enzyme solution was loaded onto a Butyl-TOYOPEARL 650M column (diameter: 4.7 cm, height: 7.7 cm) which had previously been equilibrated with a 20 mM potassium phosphate buffer (pH7.5) containing 65% ammonium sulfate; and thereby allowing the enzyme is absorbed therein. This column was washed with the same buffer solution, and then the enzyme was allowed to be eluted with 20 mM potassium phosphate buffer (pH7.5) containing 30% ammonium sulfate to collect an active fraction. The enzyme was further eluted by a gradient elution starting from the same buffer to 20 mM potassium phosphate buffer (pH7.5), and pooled with the former active fraction.

2.3. Purification by DEAE-CELLULOFINE A-500 (SEIKAGAKU KOGYO)

The abovementioned active fraction was concentrated through an ultrafiltration membrane "Pellicon 2 Module", desalted, and equilibrated with a 15 mM Tris-HCl buffer (pH8.5). This fraction was loaded onto a DEAE-CELLULOFINE A-500 column (diameter: 4.7 cm, height: 5.2 cm) which had previously been equilibrated with the same buffer solution, and the eluate was collected.

2.4 Purification by Butyl-TOYOPEARL 650M (TOSOH) (Second Process)

The abovementioned eluate was prepared in 65%-saturated ammonium sulfate (pH7.5), and centrifuged to obtain a supernatant. This supernatant was loaded onto a Butyl-TOYOPEARL 650M column (diameter: 4.7 cm, height: 3.6 cm) which had previously been equilibrated with a 20 mM potassium phosphate buffer (pH7.5) containing 65% ammonium sulfate; thereby allowing the enzyme is absorbed. This column was washed with the same buffer solution, and then the enzyme was allowed to be eluted with 20 mM potassium phosphate buffer (pH7.5) containing 30% ammonium sulfate to collect an active fraction.

2.5 Purification by TSKgel G3000SW (TOSOH)

The abovementioned active fraction was concentrated through a pencil type membrane concentration module "ACP-0013" (ASAHI KASEI), desalted, and equilibrated with 50 mM potassium phosphate buffer (pH5.5) containing 0.2M sodium chloride. This fraction was loaded onto a TSKgel G3000SW (diameter: 2.15 cm, height: 60 cm) which had previously been equilibrated with the buffer described above, and the enzyme was eluted with the same buffer to obtain an active fraction. The active fraction was concentrated through a centriplus 10 (Amicon), desalted, and transferred into a 50 mM citric acid-sodium phosphate buffer (pH5.5). The resultant enzyme approximately had a specific activity of 1,100 unit/mg, and a purification degree of about 170 times greater than that of the crude enzyme solution.

Example 3

Test of Characteristics of Coenzyme-Binding Glucose Dehydrogenase

The coenzyme-binding glucose dehydrogenase isolated in Example 2 described above was examined for its effect, optimum pH, pH for stability, optimum temperature, thermal stability, substrate specificity, molecular weight, inhibitor and coenzyme.

3.1 Effect

The coenzyme-binding glucose dehydrogenase was reacted with 500 mM D-glucose in the presence of 8.66 mM DCIP, and the reaction product was quantified using D-gluconic acid/D-glucono-δ-lactone measurement kit. As a result, the production of D-gluconic acid was identified, and it was revealed that the inventive coenzyme-binding glucose dehydrogenase is the enzyme that catalyzes a reaction for oxidizing a hydroxyl group in the 1-position of D-glucose.

3.2 Optimum pH

The buffer solution according to the Enzymatic activity measurement method 2 was replaced with the citric acid-sodium phosphate buffer (pH4.0 to 5.5), potassium phosphate buffer (pH6.5 to 7.5), Tris-HCl buffer (pH8.0 to 9.0) or glycine-sodium hydroxide buffer (pH9.5 to 10.0) (each 17 mM as a final concentration), and the enzymatic activity of the purified enzyme was measured at various pH ranges similarly to Enzymatic activity measurement method 2 (FIG. 1). As a result, the optimum pH of the coenzyme-binding glucose dehydrogenase was 7.0 to 9.0.

3.3 pH for Stability

Figure 2:
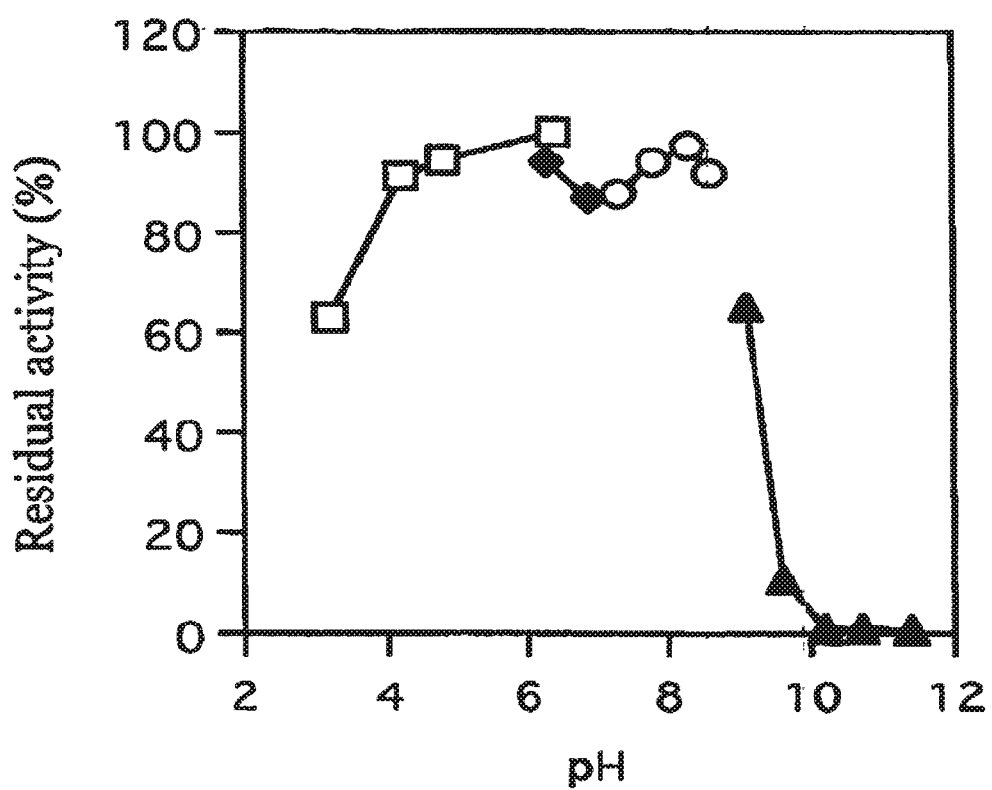
FIG. 2 shows a graph representing the relationship between the residual activity (%) of the coenzyme-binding glucose dehydrogenase and the pH, in Example 3 (3.3). Symbols show measured values and types of buffer solutions, which are □: citric acid-sodium phosphate buffer (pH3.2 to 6.4), ♦: potassium phosphate buffer (pH6.3 to 6.9), ○: Tris-HCl buffer (pH7.3 to 8.6) and ▲: glycine-sodium hydroxide (pH9.1 to 11.4). The stable pH of the enzyme was 4.5 to 8.5.

The coenzyme-binding glucose dehydrogenase was dissolved in each 50 mM buffer, i.e., citric acid-sodium phosphate buffer (pH3.2 to 6.4), potassium phosphate buffer (pH6.3 to 6.9), Tris-HCl buffer (pH7.3 to 8.6) or glycine-sodium hydroxide buffer (pH9.1 to 11.4) and kept at 40° C. for 60 minutes, and then the enzymatic activity was examined by the method according to the activity measurement method 1, and a ratio of residual enzymatic activity was analyzed (FIG. 2). As a result, the pH for the stability of the coenzyme-binding glucose dehydrogenase was pH4.5 to 8.5.

3.4 Optimum Temperature

Figure 3:
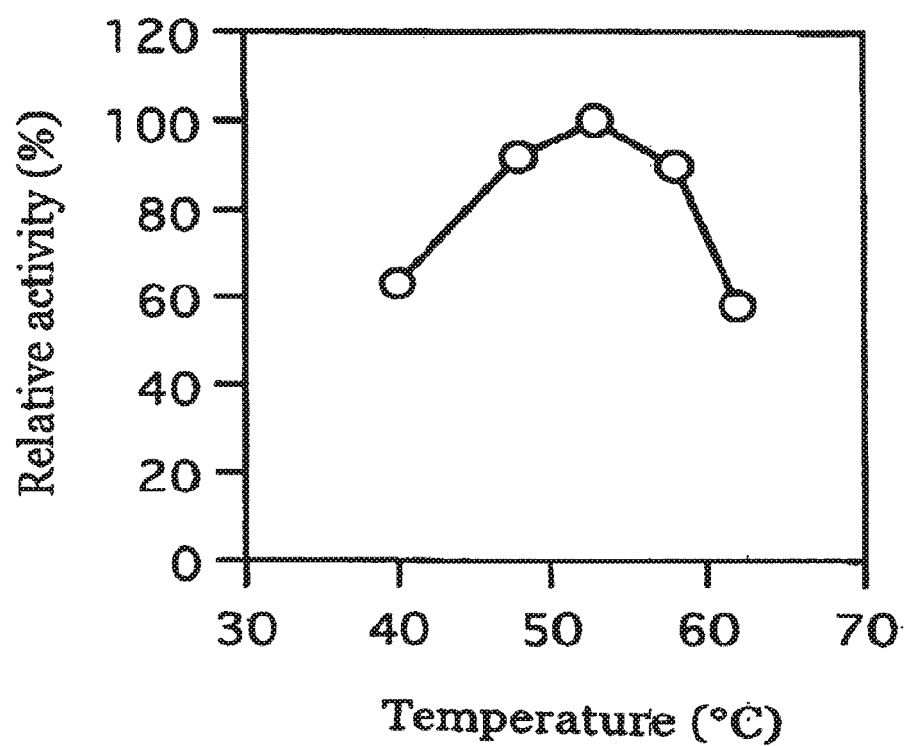
FIG. 3 shows a graph representing the relationship between the relative activity (%) of the coenzyme-binding glucose dehydrogenase and the temperature, in Example, 3 (3.4). The optimum temperature of the enzyme was approximately 55° C.

The coenzyme-binding glucose dehydrogenase was dissolved in 50 mM citric acid-sodium phosphate buffer (pH5.5) and examined for the enzymatic activity over the range from 30° C. to 62° C. by the Enzymatic activity measurement method 1 described above (FIG. 3). As a result, the optimum temperature of the coenzyme-binding glucose dehydrogenase was about 55° C.

3.5 Thermal Stability

Figure 4:
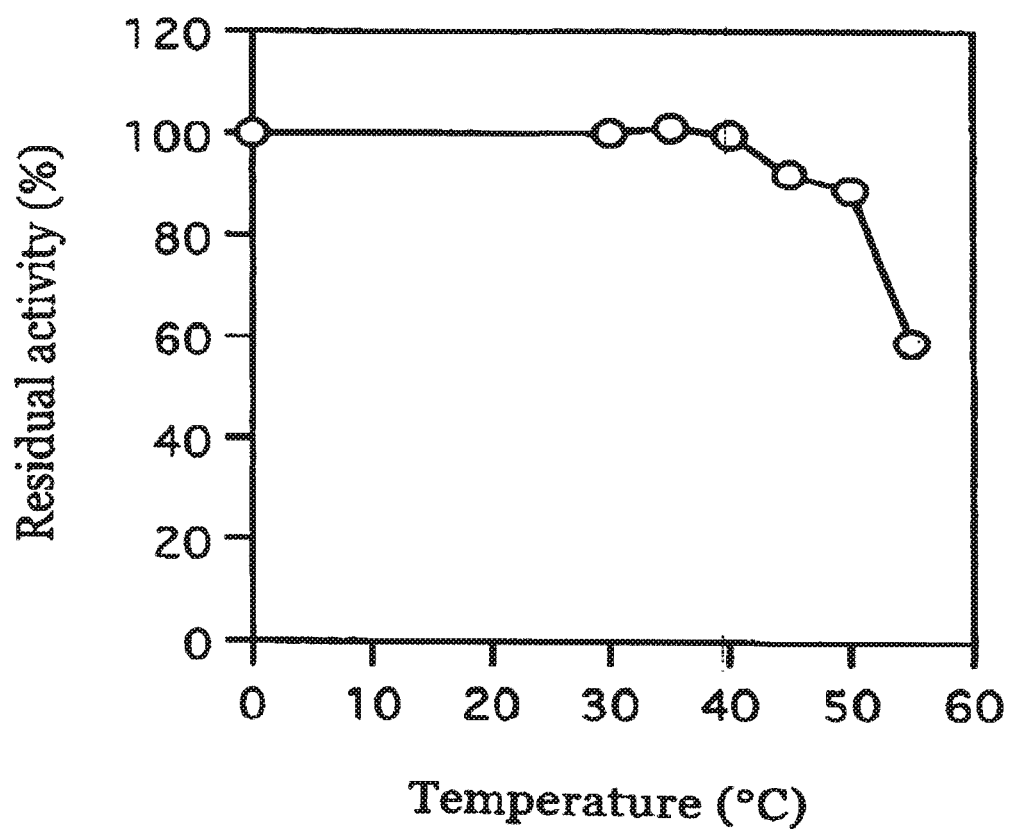
FIG. 4 shows a graph representing the relationship between the residual activity (%) of the coenzyme-binding glucose dehydrogenase in Example 3 (3.5) and the treatment temperature. The enzyme was revealed to be stable at 50° C. or below.

The coenzyme-binding glucose dehydrogenase was dissolved in 50 mM citric acid-sodium phosphate buffer (pH5.5), kept at several points of the temperature ranging from 0° C. to 55° C. for 15 minutes, and then examined for the enzymatic activity by the Enzymatic activity measurement method 1, and the ratio (%) of residual enzymatic activity was analyzed (FIG. 4). The ratio (%) of residual enzymatic activity was calculated with regarding the enzymatic activity after keeping at 0° C. for 15 minutes as 100%. As a result, the coenzyme-binding glucose dehydrogenase kept its enzymatic activity at a level as high as 89% even at 50° C., showing the stability at about 50° C. or below.

3.6 Substrate Specificity and Km Value

Employing each of D-glucose and other substrates (each at 333 mM as a final concentration, except for D-cellobiose at 193 mM, D-trehalose and D-raffinose at 121 mM), the enzymatic activity of this enzyme was measured by the Enzymatic activity measurement method 1. The activity on each substrate is represented as a relative value to the activity of this enzyme on D-glucose being regarded as 100%, and shown in Table 1.

Similarly, the relative reactivities (enzymatic activity) on D-glucose and maltose each at two final concentrations, i.e. 550 mM and 100 mM, were measured. The results are represented as relative values based on the value on D-glucose.

As evident from these results, the coenzyme-binding glucose dehydrogenase acts potently on D-glucose, and weakly on D-mannose, 1,5-anhydro-D-glucitol, D-cellobiose, D-trehalose, maltose, D-galactose, D-glucose-6-phosphate and D-fructose. This enzyme exhibited almost no effect on L-arabinose, lactose, D-sorbitol, gluconic acid, sucrose, D-mannitol, L-sorbose, D-ribose, L-rhamnose, D-glucose-1-phosphate, D-raffinose, ethanol or glycerol. The Km value of this enzyme was 49.7 mM on D-glucose.

TABLE 1

| Substrate | Relative activity (%) |
| --- | --- |
| D-Glucose | 100 |
| 2-Deoxy-D-glucose | 48 |
| D-Xylose | 9.1 |
| D-Mannose | 2.8 |
| 1,5-Anhydro-D-glucitol | 2 |
| D-Cellobiose | 2 |
| D-Trehalose | 1.7 |
| Maltose | 1.4 |
| D-Galactose | 1.2 |
| D-Glucose-6-phosphate | 1.1 |
| D-Fructose | 0.86 |
| L-Arabinose | 0.1> |
| Lactose | 0.1> |
| D-Sorbitol | 0.1> |
| Gluconic acid | 0.1> |
| Sucrose | 0.1> |
| D-Mannitol | 0.1> |
| L-Sorbose | 0.1> |
| D-Ribose | 0.1> |
| L-Rhamnose | 0.1> |
| D-Glucose-1-phosphate | 0.1> |
| D-Raffinose | 0.1> |
| Ethanol | 0.1> |
| Glycerol | 0.1> |

TABLE 2

| Substrate | Final Conc.(mM) | Relative activity (%) |
| --- | --- | --- |
| D-Glucose | 550 | 100 |
| Maltose | 550 | 2.8 |
| D-Glucose | 100 | 100 |
| Maltose | 100 | 0.5 |

3.7 Molecular Weight and Subunit Molecular Weight

The coenzyme-binding glucose dehydrogenase was dissolved in a 50 mM potassium phosphate buffer (pH7.5) containing 0.2M NaCl, and analyzed on a TSKgel-G3000SW (diameter: 0.75 cm, length: 60 cm, TOSOH) using the same buffer solution as a mobile phase. When using a molecular weight marker (Oriental Yeast) as an index, the molecular weight of the coenzyme-binding glucose dehydrogenase was revealed to be about 130 kDa. Using a 12.5% polyacrylamide gel, the inventive coenzyme-binding glucose dehydrogenase was subjected to an SDS-polyacrylamide gel electrophoresis (SDS-PAGE) according to the method by Laemmli et al (Nature, (1970) 227:680-685). After the running, the gel was stained with Coomassie brilliant blue, and the mobility was compared with that of the molecular weight marker (Amersham Pharmacia Biotech), which revealed that the subunit molecular weight of the inventive coenzyme-binding glucose dehydrogenase was about 85 kDa.

3.8 Inhibitor

Each of the various additives shown in Table 3 was added as an inhibitor at 1 mM as a final concentration to the reaction system of the Enzymatic activity measurement method 1, and the activity of the coenzyme-binding glucose dehydrogenase was measured by the Enzymatic activity measurement method 1. In a control group, the procedure similar to that of Enzymatic activity measurement method 1 was conducted except for adding no additives shown in Table 3. Based on the enzymatic activity observed in the control group being regarded as 100%, the activity in the presence of each additive was calculated as a relative activity, the difference of which from the control group activity was regarded as a % inhibitory effect. As a result, the inhibitory effect shown in Table 3 was observed.

On the other hand, in the Enzymatic activity measurement method 1 described above, 1,10-phenanthroline respectively dissolved in methanol at 1 mM, 5 mM, 10 mM, 25 mM and 50 mM as final concentrations was added, and the activity of the inventive coenzyme-binding glucose dehydrogenase was measured in accordance with the Enzymatic activity measurement method 1. The final concentration of methanol relative to each reaction system was 10% (v/v). In a control group, methanol was added in the Enzymatic activity measurement method 1 at 10% (v/v) as a final concentration. The results are shown in Table 4. It was revealed that the inhibitory effect of 1,10-phenanthroline was as high as 62.0% at 1 mM, 76% at 5 mM, 85% at 10 mM, 91% at 25 mM and 95% at 50 mM as final concentrations of 1,10-phenanthroline.

The inhibitory effect on the inventive coenzyme-binding glucose dehydrogenase varied depending on the type of the additive, and was the highest in the presence of heavy metal ion (such as $Ag^+$, $Cu^{2+}$ and $Hg^{2+}$), and was 60% or more in the presence of 1,10-phenanthroline, proflavin and $Mn^{2+}$.

TABLE 3

| Additive | Inhibition (%) |
|---|---|
| None | 0 |
| $NaN_3$ | 0 |
| $ZnCl_2$ | 0 |
| $AlCl_3$ | 0 |
| Benzoic acid | 0 |
| EDTA | 0.4 |
| $CdCl_2$ | 0.8 |
| LiCl | 0.9 |
| Aminoguanidine sulfate | 1.1 |
| $H_2O_2$ | 1.7 |
| N-Ethylmaleimide | 1.8 |
| Urea | 1.9 |
| NaCl | 2.5 |
| Tirone | 2.5 |
| $BaCl_2$ | 2.6 |
| $PbCl_2$ | 2.7 |
| $MgCl_2$ | 2.8 |
| Fumaric acid | 3.4 |
| Cycloserine | 3.6 |
| DL-Penicillamine | 4.3 |
| Meso-tartaric acid | 5.6 |
| Citric acid | 5.6 |
| $CaCl_2$ | 5.7 |
| Quinacrine | 5.0 |
| TritonX-100 | 6.2 |
| $CoCl_2$ | 7.0 |
| Malic acid | 8.1 |
| D-Tartaric acid | 8.5 |
| Iodoacetic acid | 9.5 |
| Cysteamine | 9.8 |
| 2,2'-Bipyridine | 10.8 |
| 8-Quinolinol | 13.9 |
| KCN | 14.5 |
| $NiCl_2$ | 16.5 |
| $FeCl_3$ | 25.0 |
| Maleic acid | 26.2 |
| Acrinol | 29.0 |
| 2-Nitrobenzoic acid | 44.3 |
| $SnCl_2$ | 45.5 |
| Acriflavine | 49.0 |
| 1,10-Phenanthroline | 62.0 |
| Proflavin | 62.0 |
| $MnCl_2$ | 75.5 |
| $AgNO_3$ | 99.4 |
| $CuCl_2$ | 100 |
| $HgCl_2$ | 100 |

TABLE 4

| Final concentration of 1,10-phenanthroline (mM) | Inhibit (%) |
|---|---|
| 0 | 0 |
| 50 | 95 |
| 25 | 91 |
| 10 | 85 |
| 5 | 76 |

3.9. Coenzyme

The inventive coenzyme-binding glucose dehydrogenase solution was supplemented with D-glucose and subjected to the absorption analysis, which indicated the disappearance of the maximum absorptions observed at 385 nm and 465 nm in response to the supplement, revealing that the coenzyme was flavin adenine dinucleotide. These maximum absorptions are specific to FAD, and it was not observed in a control group reaction system constructed by excluding FAD only.

Example 4

Glucose Quantification

Figure 5:
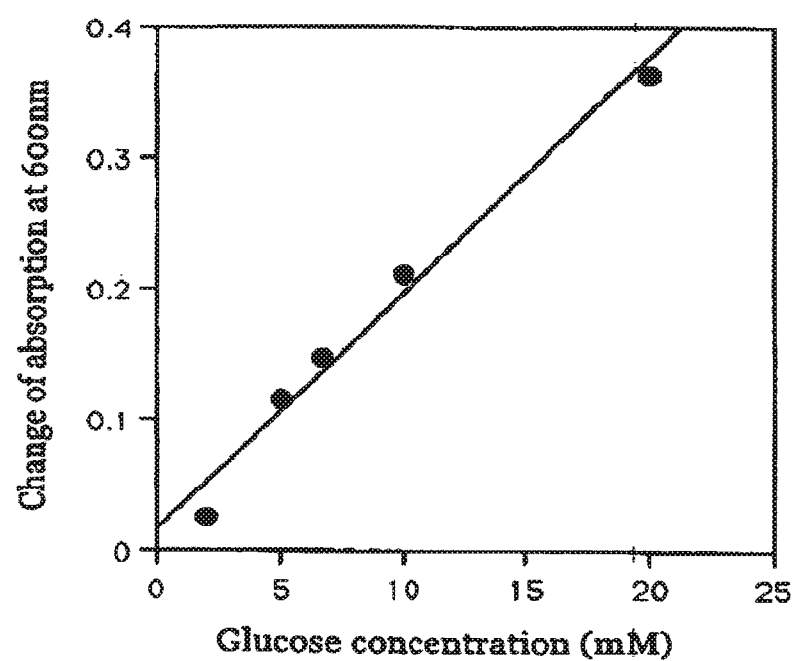
FIG. 5 shows a calibration curve for quantifying the glucose in Example 4, which indicates the change in DCIP absorption vs the glucose level.

The coenzyme-binding glucose dehydrogenase derived from the deposited strain 97508 purified in Example 2 described above was employed, and the absorption reduction rate was measured using D-glucose at the concentration ranging from 0.333 to 33 mM instead of 333 mM D-glucose in the Enzymatic activity measurement method 1. Thus, the transition in the absorption was measured at each D-glucose concentration of 0.333 mM, 0.5 mM, 1 mM, 2 mM, 5 mM, 6.67 mM, 10 mM, 20 mM and 33 mM. The results of the measurement are shown in FIG. 5.

As a result, a calibration curve (correlation coefficient r=0.997) was obtained; thereby, it was apparent that the quantification of D-glucose employing the coenzyme-binding glucose dehydrogenase is possible.

Example 5

Measurement of Glucose by Enzyme-Immobilizing Electrode

Figure 6:
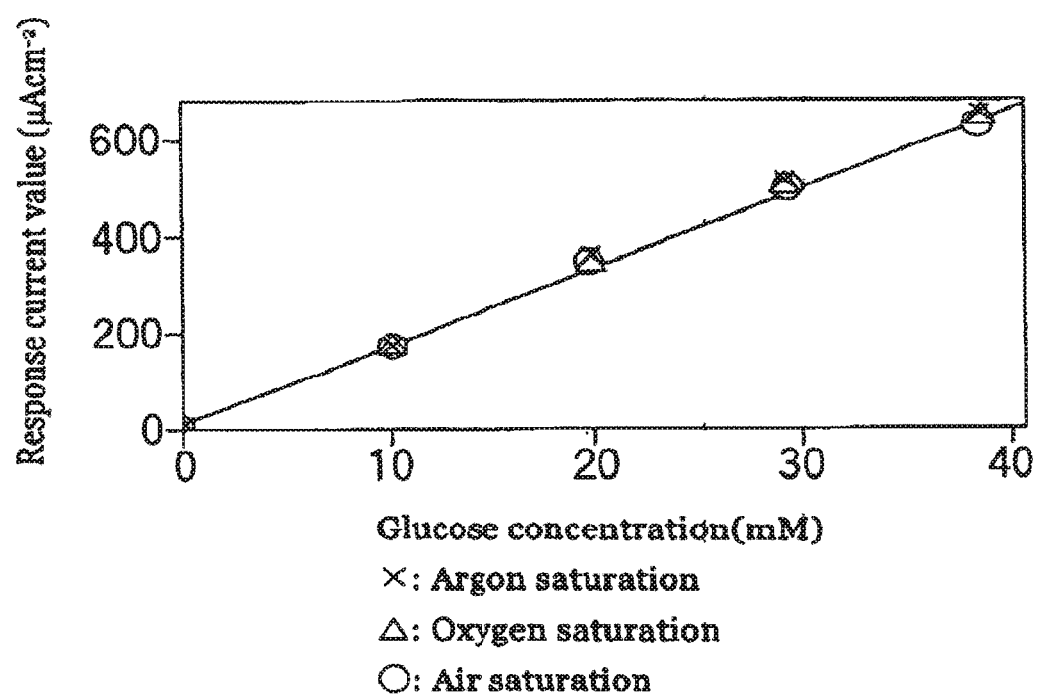
FIG. 6 shows a calibration curve for a glucose measurement using a coenzyme-binding glucose dehydrogenase-immobilizing electrode in Example 5. Symbols represent the conditions under: x: argon saturation, Δ: oxygen saturation and ○: air saturation.

The coenzyme-binding glucose dehydrogenase derived from the deposited strain 97508 purified in Example 2 described above was employed to measure D-glucose by an enzyme-immobilizing electrode. A glassy carbon (GC) electrode on which 3.4 U of this enzyme was immobilized was employed to measure the response current to the glucose concentration. In an electrolytic cell, 2.7 ml of 100 mM sodium phosphate buffer (pH7.0) and 0.3 ml of 1M aqueous solution of potassium hexacyanoferrate (III) (potassium ferricyanide) were added. The GC electrode was connected to the potentiostat BAS100B/W (BAS), and the solution was stirred at 40° C. in each condition of argon saturation, oxygen saturation and air saturation while applying +500 mV to the silver-silver chloride reference electrode. 30 µl of a 1M D-glucose solution was added to these systems, and the current value in the stationary phase was measured. The same amount of the 1M D-glucose solution was further added, and the current value was measured, these procedure being repeated each three times. The resultant current values vs the known glucose concentrations (about 10, 20, 30 and 40 mM) were plotted to obtain a calibration curve (FIG. 6). Thereby, it was apparent that the quantification of glucose by the enzyme-immobilizing electrode employing the coenzyme-binding glucose dehydrogenase is possible. It was also revealed, based on the consistent calibration curve obtained regardless of any gas saturated conditions, that the coenzyme-binding glucose dehydrogenase is extremely inert to the oxygen and that it is possible to quantify D-glucose by the enzyme-immobilizing electrode utilizing the enzyme without being subjected to any effect of the oxygen.

Example 6

Measurement of Glucose in Standard Serum by Enzyme-Immobilizing Electrode

Analogous to Example 5, the concentration of glucose in a serum was measured by the enzyme-immobilizing electrode using the control serum I WAKO B (WAKO PURE CHEMICAL). In an electrolytic cell, 2.4 ml of 100 mM sodium phosphate buffer (pH7.0) and 0.3 ml of 1M aqueous solution of potassium hexacyanoferrate (III) (potassium ferricyanide) were added, and the serum was added when the current value became stationary and the current value was measured. Similarly, the D-glucose solutions of known concentrations were measured to obtain a calibration curve.

The glucose concentration in the serum was identified by the calibration curve method to be 4.5 mM, which was in agreement with the concentration of the glucose identified by the hexokinase-glucose-6-phosphate dehydrogenase method. Accordingly, it was revealed that the quantification of D-glucose in serum by the enzyme-immobilizing electrode employing the coenzyme-binding glucose dehydrogenase employed in the invention is possible.

INDUSTRIAL APPLICABILITY

According to the present invention, it became possible to provide a soluble coenzyme-binding glucose dehydrogenase whose activity on altose is 5% or less and which is inhibited by 1,10-phenanthroline. Furthermore, a method for producing the coenzyme-binding glucose dehydrogenase suitable to an industrial production and a microorganism producing therefor are also provided. As a result, it becomes possible to apply the coenzyme-binding glucose dehydrogenase to an industrial application, and more particularly, it becomes possible to measure the blood sugar level even in a diabetes patient receiving an infusion containing maltose. Also by using the inventive coenzyme-binding glucose dehydrogenase, a trace amount of the glucose can be measured even with a glucose sensor, thus enabling the utility. It also becomes possible to use in a material production or analysis including a method for measuring or eliminating glucose in a sample using the coenzyme-binding glucose dehydrogenase as well as a method for producing an organic compound, thereby providing a highly utilizable enzyme, which enables use for modifying a material in the fields of pharmaceuticals, clinical studies and food products.

The invention claimed is:

1. A biosensor for measuring glucose in a sample liquid comprising:
    an electrode system comprising an action electrode and a counter electrode; and an enzymatic reaction layer in contact with the action electrode and/or the counter electrode, the enzymatic reaction layer comprising an electron acceptor and a soluble flavin adenine dinucleotide-binding glucose dehydrogenase (FAD-GDH) obtained from *Aspergillus* wherein the flavin adenine dinucleotide-binding glucose dehydrogenase is secreted from an *Aspergillus* fungal body and has enzymatic activity to glucose comprising catalyzing a reaction for oxidizing glucose in the presence of the electron acceptor,
    wherein enzymatic activity of the FAD-GDH to maltose is 5% or less relative to the enzymatic activity of the FAD-GDH to glucose, and wherein enzymatic activity of the FAD-GDH to D-fructose is not more than the enzymatic activity of the FAD-GDH to maltose, and wherein the biosensor is capable of quantifying glucose concentrations ranging from 4.5 mM to 30 mM.
2. The biosensor of claim 1, wherein the enzymatic activity to maltose is 3% or less relative to the enzymatic activity to glucose.

* * * * *